(12) United States Patent
Kshirsagar et al.

(10) Patent No.: US 10,308,669 B2
(45) Date of Patent: Jun. 4, 2019

(54) LAMINATED ARTICLES FOR MICROBIAL REMOVAL AND LOW PRESSURE DROP FILTRATION, METHODS OF MAKING, AND METHODS OF USING SAME

(71) Applicant: 3M INNOVATIVE PROPERTIES COMPANY, St. Paul, MN (US)

(72) Inventors: Manjiri T. Kshirsagar, Woodbury, MN (US); Bong Y. Yeom, Woodbury, MN (US); Timothy J. Rowell, St. Paul, MN (US); Satinder K. Nayar, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 389 days.

(21) Appl. No.: 15/037,132

(22) PCT Filed: Dec. 12, 2014

(86) PCT No.: PCT/US2014/069904
§ 371 (c)(1),
(2) Date: May 17, 2016

(87) PCT Pub. No.: WO2015/094938
PCT Pub. Date: Jun. 25, 2015

(65) Prior Publication Data
US 2016/0289249 A1    Oct. 6, 2016

Related U.S. Application Data

(60) Provisional application No. 61/918,206, filed on Dec. 19, 2013.

(51) Int. Cl.
| | |
|---|---|
| *B01D 39/00* | (2006.01) |
| *C07F 7/08* | (2006.01) |
| *C07F 7/18* | (2006.01) |
| *B01D 39/14* | (2006.01) |
| *D04H 13/00* | (2006.01) |
| *B01D 39/16* | (2006.01) |
| *B01D 39/20* | (2006.01) |
| *B32B 5/02* | (2006.01) |
| *B32B 27/12* | (2006.01) |
| *B32B 27/32* | (2006.01) |
| *B32B 27/34* | (2006.01) |
| *B32B 27/36* | (2006.01) |
| *B01D 39/08* | (2006.01) |
| *B32B 27/00* | (2006.01) |

(52) U.S. Cl.
CPC ......... *C07F 7/0836* (2013.01); *B01D 39/086* (2013.01); *B01D 39/14* (2013.01); *B01D 39/1623* (2013.01); *B01D 39/2031* (2013.01); *B32B 5/022* (2013.01); *B32B 27/12* (2013.01); *B32B 27/32* (2013.01); *B32B 27/34* (2013.01); *B32B 27/36* (2013.01); *C07F 7/0838* (2013.01); *C07F 7/1804* (2013.01); *D04H 13/00* (2013.01); *B01D 2239/0442* (2013.01); *B01D 2239/0654* (2013.01); *B32B 2264/102* (2013.01)

(58) Field of Classification Search
USPC ....... 210/656, 660, 679, 681, 767, 263, 483, 210/496, 503, 502.1, 504, 506, 507, 508
See application file for complete search history.

(56) References Cited

U.S. PATENT DOCUMENTS

| | | | | |
|---|---|---|---|---|
| 4,415,631 | A | * 11/1983 | Schutijser | ............. C08F 292/00 |
| | | | | 210/198.2 |
| 4,772,488 | A | 9/1988 | Pinch | |
| 5,605,746 | A | 2/1997 | Groeger | |
| 5,910,137 | A | * 6/1999 | Clark | ................... A61F 13/505 |
| | | | | 604/385.04 |
| 5,998,032 | A | * 12/1999 | Hansen | ............... A61F 13/0209 |
| | | | | 428/296.1 |
| 6,015,582 | A | 1/2000 | Kageyama | |
| 6,031,119 | A | 2/2000 | Lee et al. | |
| 6,045,913 | A | 4/2000 | Castle | |
| 6,127,595 | A | 10/2000 | Makoui | |
| 6,458,442 | B1 | * 10/2002 | McKay | ................ A47L 23/266 |
| | | | | 15/104.93 |
| 2008/0233850 | A1 | 9/2008 | Woo | |
| 2010/0209961 | A1 | 8/2010 | Kshirsagar | |
| 2010/0326902 | A1 | 12/2010 | Midkiff | |
| 2012/0241391 | A1 | 9/2012 | Carlson | |

FOREIGN PATENT DOCUMENTS

| | | |
|---|---|---|
| CN | 101411958 | 4/2009 |
| CN | 101836655 | 9/2010 |
| JP | 06-184996 | 7/1994 |

(Continued)

OTHER PUBLICATIONS

"Standard for Hygienic Safety Evaluation of Equipment and Protective Materials in Drinking Water," (standard No. GB/T 17219-1998), 3 pages.

(Continued)

*Primary Examiner* — Allison G Fitzsimmons
(74) *Attorney, Agent, or Firm* — Adrian L. Pishko

(57) ABSTRACT

Laminated articles are provided including a porous fibrous nonwoven matrix and guanidine-functionalized metal silicate particles enmeshed within the porous fibrous nonwoven matrix. The laminated articles further include a first substrate and a second substrate sealed to the first substrate. Methods of making laminated articles and methods of using laminated articles are also provided.

15 Claims, No Drawings

(56) References Cited

FOREIGN PATENT DOCUMENTS

| | | |
|---|---|---|
| JP | 07-017816 | 1/1995 |
| JP | 08-176527 | 7/1996 |
| JP | H09276897 | 10/1997 |
| JP | 11-1556 | 1/1999 |
| WO | WO 2008-072113 | 6/2008 |
| WO | WO 2011-109151 | 9/2011 |
| WO | WO 2012-078374 | 6/2012 |
| WO | WO 2012-078426 | 6/2012 |
| WO | WO 2013-184366 | 12/2013 |
| WO | WO 2014-088807 | 6/2014 |
| WO | WO 2015-047464 | 4/2015 |
| WO | WO 2015-095100 | 6/2015 |

OTHER PUBLICATIONS

International Search report for PCT International Application No. PGT/US2014/069904 dated Mar. 27, 2015, 4 pages.

\* cited by examiner

LAMINATED ARTICLES FOR MICROBIAL REMOVAL AND LOW PRESSURE DROP FILTRATION, METHODS OF MAKING, AND METHODS OF USING SAME

CROSS REFERENCE TO RELATED APPLICATIONS

This application is a national stage filing under 35 U.S.C. 371 of PCT/US2014/069904, filed Dec. 12, 2014, which claims the benefit of U.S. Application No. 61/918,206, filed Dec. 19, 2013, the disclosure of which is incorporated by reference in its/their entirety herein.

BACKGROUND

Microbial removal for purposes such as purification, isolation, detection, and the like, has long been an objective of investigators.

SUMMARY

In broad summary, herein are disclosed laminated articles for microbial removal and low pressure drop filtration, methods of making, and methods of using such laminated articles.

In a first aspect, the present disclosure provides a laminated article. The laminated article includes a porous fibrous nonwoven matrix and a plurality of guanidine-functionalized metal silicate particles enmeshed within the porous fibrous nonwoven matrix, a first substrate, and a second substrate sealed to the first substrate. The guanidine-functionalized metal silicate particles include a metal silicate particle that is modified with at least one silane having the formula $X_{3-n}R^a{}_nSi\text{—}Y\text{-}G$, wherein: n is 0, 1, or 2; each $R^a$, if present, is independently an alkyl, aralkyl, or aryl; Y is a divalent group comprising an alkylene having 2 to 20 carbons; G is a guanidine group of the formula $\text{—NH—C}(\text{=NH})\text{—NH}_2$; and each X is independently alkoxy or acyloxy. The second substrate is sealed to the first substrate along at least a portion of a perimeter of the first substrate, and the (particle-containing) porous fibrous nonwoven matrix is disposed between the first substrate and the second substrate.

In a second aspect, the present disclosure provides a method of making a laminated article. The method includes: (a) providing a plurality of fibers; (b) providing a plurality of guanidine-functionalized metal silicate particles; (c) mixing the plurality of guanidine-functionalized metal silicate particles and the plurality of fibers together to form a porous fibrous nonwoven matrix having the guanidine-functionalized metal silicate particles enmeshed within the porous fibrous nonwoven matrix; (d) providing a first substrate; (e) providing a second substrate; (f) disposing the porous fibrous nonwoven matrix having the guanidine-functionalized metal silicate particles between the first substrate and the second substrate; and (g) sealing the second substrate to the first substrate along at least a portion of a perimeter of the first substrate.

In a third aspect, the present disclosure provides a method of removing microorganisms from an aqueous sample. The method includes: (a) providing a laminated article according the first aspect of the present disclosure; (b) providing a fluid sample containing at least one microorganism strain; and (c) contacting the laminated article with the fluid sample such that at least a portion of the at least one microorganism strain is removed from the fluid sample.

In a fourth aspect, the present disclosure provides a filtration device. The filtration device includes a container having inlet and outlet ports for liquid passage, and a laminated article according to the first aspect of the present disclosure contained within the container.

In some embodiments of any of the above aspects of the present disclosure, the guanidine-functionalized metal silicate particles are guanidine-functionalized magnesium silicate particles; in some embodiments, the guanidine-functionalized metal silicate particles are amorphous; in some embodiments, the guanidine-functionalized metal silicate particles are amorphous, spheroidized particles; and in some embodiments, the guanidine-functionalized metal silicate particles are amorphous guanidine-functionalized magnesium silicate particles.

These and other aspects of the invention will be apparent from the detailed description below. In no event, however, should the above summary be construed to limit the claimable subject matter, whether such subject matter is presented in claims in the application as initially filed or in claims that are amended or otherwise presented in prosecution.

DETAILED DESCRIPTION

In the following detailed description, various sets of numerical ranges (for example, of the number of carbon atoms in a particular moiety, of the amount of a particular component, or the like) are described, and, within each set, any lower limit of a range can be paired with any upper limit of a range. Such numerical ranges also are meant to include all numbers subsumed within the range (for example, 1 to 5 includes 1, 1.5, 2, 2.75, 3, 3.80, 4, 5, and so forth).

As used herein, the term "and/or" means one or all of the listed elements or a combination of any two or more of the listed elements.

The words "preferred" and "preferably" refer to embodiments of the present disclosure that may afford certain benefits under certain circumstances. Other embodiments may also be preferred, however, under the same or other circumstances. Furthermore, the recitation of one or more preferred embodiments does not imply that other embodiments are not useful, and is not intended to exclude other embodiments from the scope of the invention.

The term "comprises" and variations thereof do not have a limiting meaning where these terms appear in the description and claims.

As used herein, "a," "an," "the," "at least one," and "one or more" are used interchangeably.

As used in this patent application:

"enmeshed" (in regard to particles in a fibrous nonwoven matrix) means that the particles are entrapped in the fibrous nonwoven matrix (and, preferably, distributed within it), rather than merely being borne on its surface;

"fibrillated" (in regard to fibers or fibrous material) means treated (for example, by beating) in a manner that forms fibrils or branches attached to a fiber's main trunk;

"fibrous nonwoven matrix" means a web or medium, other than a woven or knitted fabric, comprising interlaid fibers (for example, a web comprising fibers that are interlaid by meltblowing, spunbonding, or other air laying techniques; carding; wet laying; or the like);

"laminated" means an article having a plurality of stacked layers (for example, an article having a first substrate layer, a fibrous nonwoven matrix layer disposed on the first substrate layer, and a second substrate layer disposed on the fibrous nonwoven matrix layer);

"microorganism" means any cell or particle having genetic material suitable for analysis or detection (including, for example, bacteria, yeasts, viruses, and bacterial endospores);

"microorganism strain" means a particular type of microorganism that is distinguishable through a detection method (for example, microorganisms of different genera, of different species within a genus, or of different isolates within a species);

"polygon" means a shape having three or more sides;

"porous" means permeable by liquids;

"sample" means a substance or material that is collected (for example, to be analyzed);

"sample matrix" means the components of a sample other than microorganisms; and

"through pore" (in reference to a porous matrix) means a pore that comprises a passageway or channel (with separate inlet and outlet) through the porous matrix.

A laminated article of the present disclosure includes a porous fibrous nonwoven matrix, a plurality of particles enmeshed within the porous fibrous nonwoven matrix, and first and second substrates. The (particle-containing) porous fibrous nonwoven matrix is disposed between the first substrate and the second substrate, and the second substrate is sealed to the first substrate along at least a portion of a perimeter of the first substrate. The laminated article allows liquid to flow through the substrates and porous fibrous nonwoven matrix, and to contact the enmeshed particles.

The particles are guanidine-functionalized metal silicate particles. A guanidine-functionalized metal silicate particle comprises at least one guanidine-containing ligand. The guanidine-containing ligand is formed by modifying the metal silicate particle with a guanidine-containing silane having the structure shown in Formula 1:

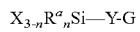  Formula 1

In Formula 1, Si is a silicon atom, and G denotes a guanidine group of the formula —NH—C(=NH)—NH$_2$. Y is a divalent group that is covalently bonded to the silicon atom at one end and to the G group at the other end. Each R$^a$ group, if any are present, is independently an alkyl, aralkyl, or aryl group, and is attached to the silicon atom. Each X is a leaving group covalently bonded to the silicon atom and is independently alkoxy or acyloxy, and n is 0, 1, or 2.

A typical alkylene can be up to 20, up to 16, 12, 10, 8, 7, 6, 5, 4, or even up to 3 carbons, or even 2 carbons, inclusive of the terminal atoms of the divalent group. In some embodiments, Y is a divalent group comprising an alkylene of 3 to 6 carbons. In a preferred embodiment, Y is a divalent group having 3 carbons (i.e., propyl).

In Formula 1, each leaving group X is independently an alkoxy group of 1, 2, 3, 4, 5, 6, 7, 8, 9, or even up to 10 carbons, or is an acyloxy group of 2 carbons, or 3, 4, 5, 6, 7, 8, 9, or even up to 10 carbons, where the alkoxy or acyloxy group is bonded to the silicon through an oxygen atom.

In some embodiments, n is 0. When n is 0, no R$^a$ groups are present, and Formula 1 can be re-written more simply as shown in Formula 2 (where Si, G, Y, and X are as defined for Formula 1):

  Formula 2

When the silane of Formula 1 (or Formula 2) reacts with an —OH group on the surface of a metal silicate particle, at least one X leaving group is replaced by a covalent bond of between the silicon atom and an oxygen atom on the surface of the metal silicate particle. An embodiment of a guanidine-functionalized metal silicate particle comprising a specific exemplary guanidine-containing ligand within the general type represented by Formula 1, wherein n=0 (i.e., as in Formula 2), is shown in Formula 3 (the circle in Formula 3 represents a metal silicate particle):

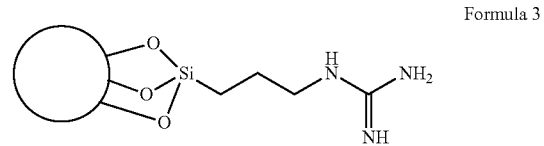

Formula 3

It will be understood that Formula 3 represents a specific embodiment wherein n is 3 and Y is a divalent group that is alkylene having 3 carbons. In each of Formulas 1 to 3, the ionization state of the guanidine group is omitted; however, it will be understood that in various environments such guanidine groups may be charged or uncharged (e.g., protonated or deprotonated), for example, according to the pH of a liquid medium in which the guanidine group is present, as discussed later herein.

The covalent bond(s) between the oxygen(s) of the ligand and the particle can be conveniently obtained, for example, by reacting a Si-bonded hydrolyzable group of the guanidine-containing precursor with a hydroxyl group of the particle, as discussed in detail later herein. While the exemplary structure of Formula 3 shows three such bonded oxygen atoms (i.e., n=3 in Formula 1), it will be appreciated that in various embodiments one, two or three such bonded oxygen atoms can be provided. If less than three such oxygen atoms are bonded to the silicon atom, other substituents (e.g., substituents that are not bonded to the particle, and which are not shown in Formula 1) may be present on the silicon atom. For example, the guanidine-containing ligand can include a polymeric structure involving formation of Si—O—Si (i.e., siloxane) groups, resulting from Si—O bonds being formed between two or more guanidine-containing ligand precursors. Without being bound by theory, it is thought that Si—O—Si groups may form in the presence of added water, or other aqueous solvents, or other agent that can hydrolyze bonds in Si—O—R groups, to give rise to more complex guanidine-containing ligand structures attached to particles, including such possible structures as shown in the non-limiting examples of Formulas 4a to 4d (each R in Formulas 4a to 4d independently being H or lower alkyl (e.g., methyl), or even another Si atom in which may or may not be attached to the metal silicate particle through an Si—O-bond; the circle in each of Formulas 4a to 4d represents a metal silicate particle):

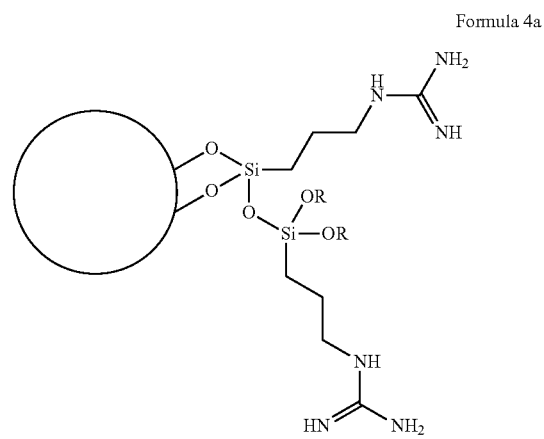

Formula 4a

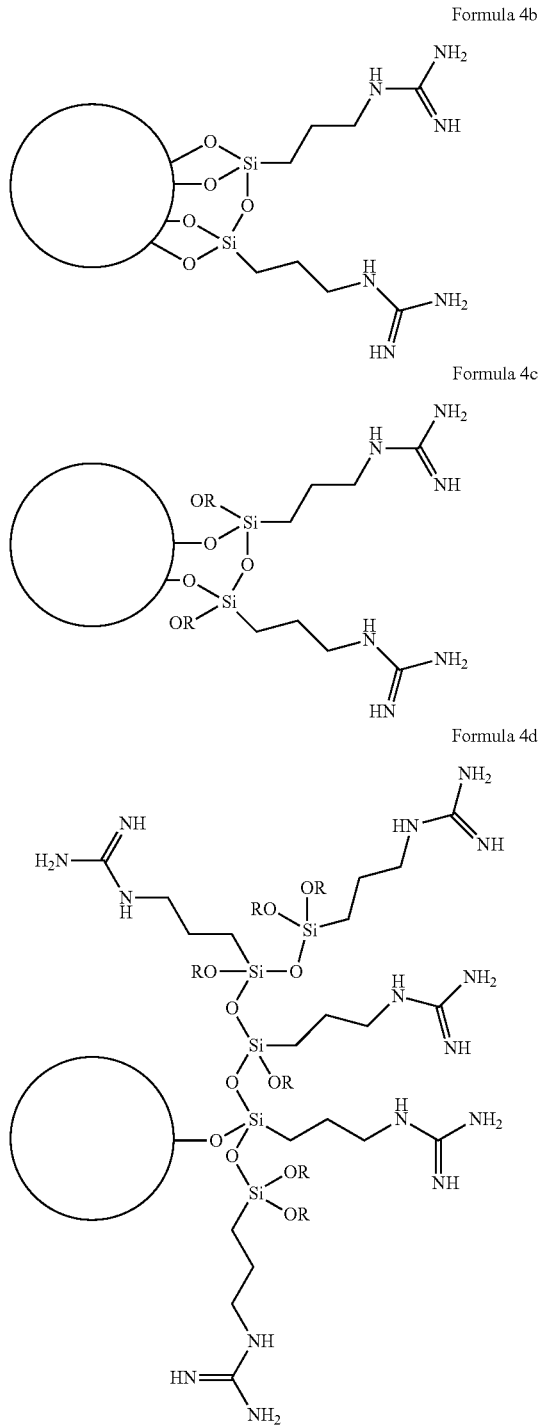

Formula 4b

Formula 4c

Formula 4d

It is seen from Formulas 4a to 4d that a network of polymerized guanidine-containing ligands can form a coating on the surface of the metal silicate particle. In some embodiments it may be desirable to obtain the particle functionalized with polymerized guanidine-containing ligand (e.g., as in any of the non-limiting polymerized guanidine-containing ligand structures shown in Formulas 4a to 4d, or the like, having at least one Si—O—Si group in the polymerized guanidine-containing ligand), as a means of increasing the loading of nitrogen-containing guanidine groups on the surface of the metal silicate particle. It is thought that in at least these types of polymerizations, a loading of nitrogen-containing guanidine groups on the surface of the metal silicate particle can attain levels of surface nitrogen content in a range from 1 to 10 atomic percent, as can be measured, for example, by X-ray photoelectron spectroscopy.

Guanidine-functionalized particles of the present disclosure include metal silicate particles. Useful metal silicates include silicates of metals such as magnesium, calcium, zinc, aluminum, iron, titanium, and the like (preferably, magnesium, zinc, iron, and titanium; more preferably, magnesium), and combinations thereof. Preferred are amorphous metal silicates in at least partially fused particulate form; more preferably, amorphous, spheroidized metal silicates; and even more preferably, amorphous, spheroidized magnesium silicate. Metal silicates are known and can be chemically synthesized by known methods or obtained through the mining and processing of raw ores that are naturally-occurring.

The metal silicate particle, and more particularly, a magnesium silicate particle, bears sufficient surface hydroxyl groups (typically, Si—OH groups) to enable a desired number of guanidine-containing ligands to be covalently attached thereto.

Amorphous, at least partially fused particulate forms of metal silicate can be prepared by any of the known methods of melting or softening relatively small feed particles (for example, average particle sizes up to about 25 micrometers) under controlled conditions to make generally ellipsoidal or spheroidal particles (that is, particles having magnified two-dimensional images that are generally rounded and free of sharp corners or edges, including truly or substantially circular and elliptical shapes and any other rounded or curved shapes). Such methods include atomization, fire polishing, direct fusion, and the like. A preferred method is flame fusion, in which at least partially fused, substantially glassy particles are formed by direct fusion or fire polishing of solid feed particles (for example, as in the method described in U.S. Pat. No. 6,045,913 (Castle et al.). Most preferably, such methods can be utilized to produce amorphous, spheroidized metal silicates by converting a substantial portion of irregularly-shaped feed particles (for example, from about 15 to about 99 volume percent; preferably, from about 50 to about 99 volume percent; more preferably, from about 75 to about 99 volume percent; most preferably, from about 90 to about 99 volume percent) to generally ellipsoidal or spheroidal particles.

Some amorphous metal silicates are commercially available. For example, amorphous, spheroidized magnesium silicate is commercially available for use in cosmetic formulations (for example, "3M COSMETIC MICROSPHERES CM-111", available from 3M Company, St. Paul, Minn.).

The guanidine-functionalized metal silicate particles used in making the laminated article of the present disclosure can be used in essentially any particulate form (preferably, a relatively dry or volatiles-free form) that is amenable to blending with fibers to form the laminated articles of the present disclosure.

Preferably, the guanidine-functionalized metal particles are used in the form of a powder. Useful powders include those that comprise microparticles (preferably, microparticles having a particle size in the range of about 1 micrometer (more preferably, about 3 micrometers; even more preferably, about 4 micrometers; most preferably, about 5 micrometers) to about 100 micrometers (more preferably, about 50 micrometers; even more preferably, about 25 micrometers; most preferably, about 15 or 20 micrometers; where any lower limit can be paired with any upper limit of the range, as referenced above).

Particularly preferred are guanidine-functionalized magnesium silicate particles. Suitable guanidine-functionalized magnesium silicate particles for use in carrying out the process of the present disclosure include those that comprise an amorphous magnesium silicate and that have a surface composition having a metal atom to silicon atom ratio greater than 0.01 and less than or equal to about 0.5 (preferably, less than or equal to about 0.4; more preferably, less than or equal to about 0.3; most preferably, less than or equal to about 0.2), as determined by X-ray photoelectron spectroscopy ("XPS", also known as Electron Spectroscopy for Chemical Analysis ("ESCA")).

XPS is a technique that can provide information about the elemental and chemical (oxidation state and/or functional group) concentrations present on a solid surface. XPS typically provides an analysis of the outermost 3 to 10 nanometers (nm) of the specimen surface. XPS is sensitive to all elements in the periodic table except hydrogen and helium with detection limits for most species in the 0.1 to 1 atomic percent concentration range. In some cases, for example for guanidine-functionalized CM-111 particles, a preferred surface composition assessment conditions for XPS can include a take-off angle of 45 degrees measured with respect to the sample surface with a solid angle of acceptance of ±10 degrees. A person skilled in the art can select a suitable instrument setting for analysis of particles of the present disclosure.

In embodiments of the present disclosure, guanidine-functionalized metal silicate particles have a surface nitrogen content in a range from 1 atomic percent to 10 atomic percent, as measured by XPS. In some embodiments, the guanidine-functionalized metal silicate particles have a surface nitrogen content of at least 1 atomic percent, at least 2, at least 3, at least 4, or even at least 5 atomic percent, as measured by XPS. In some embodiments, the guanidine-functionalized metal silicate particles have a surface nitrogen content of up to 20 atomic percent, up to 15, up to 10, up to 9, up to 8, up to 7, or even up to 6 atomic percent, as measured by XPS. The surface nitrogen content of the guanidine-functionalized metal silicate particles, as measured by XPS, may be any combination of these lower and upper values, inclusive of the values thereof. A person skilled in the art would understand that in some embodiments it may be preferred to select higher or lower surface nitrogen content within these ranges, depending on the desired application.

It will be appreciated that a guanidine group as described herein may be uncharged or charged (e.g., protonated) depending on the particular environment in which it is placed (e.g., depending on the pH of an aqueous buffer with which the guanidine-functionalized particle is brought into contact). In environments in which a guanidine group of a guanidine-functionalized particle is charged, the charged guanidine group may comprise an associated counterion. In some embodiments such a counterion may arise in the generation of the guanidine group (that is, the guanidine group as produced in the synthesis reaction may be charged, and may have a counterion associated therewith, as discussed later herein). In other embodiments a counterion may not arise in the generation of the guanidine group (e.g., the guanidine group may be produced in the synthesis reaction as a free base), but the guanidine-containing ligand (e.g., the functionalized particle) may be later placed into an environment (e.g., a liquid buffer) in which the guanidine group becomes charged and a corresponding counterion becomes associated therewith. In still other embodiments, a particular counterion may be associated with the guanidine group (e.g. as synthesized), but the counterion may then be exchanged for a different counterion. The charge state of a guanidine group and the presence and identity and charge state of a counterion thus possibly varying with environment, it is emphasized that all references to guanidine groups in the claims herein, are irrespective of the charge state of the guanidine group and are irrespective of the presence or identity of an associated counterion, unless such charge state and/or presence and/or identity of a counterion is explicitly specified in the claim.

Furthermore, the concept of a counterion that is associated with a guanidine group is used broadly herein, and it will be understood that such a counterion may not necessarily be constantly located in close proximity to the same guanidine group. Furthermore, the guanidine group and the associated counterion do not necessarily have to always be fully solvated (e.g., in aqueous solution). That is, they may be present as salts in a partially or substantially dried product (e.g., a solid or semi-solid product), which product may be placed into a liquid (e.g., an aqueous buffer) and solvated as desired. In specific embodiments, the associated counterion is a sulfate and/or bisulfate ion. In other specific embodiments, the associated counterion is a hydroxide ion (as may result, for example, from putting a guanidine group in the free-base form into an unbuffered aqueous solution).

In some embodiments, a guanidine-functionalized particle can be made by a simple and convenient method using an O-alkylisourea, or a salt thereof (for example, O-methylisourea hemisulfate, which is a readily available starting material, CAS No. 52328-05-9). In a first step of this method, an O-alkylisourea may be reacted with a linker molecule of the general structure shown in Formula 5:

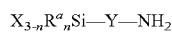

$$X_{3-n}R^a{}_n\text{Si}-Y-NH_2 \qquad \text{Formula 5}$$

In Formula 5, Si is a silicon atom, and $NH_2$ denotes a primary amino group. Y is a divalent group that is covalently bonded to the silicon atom at one end and to the primary amino group at the other end. Each $R^a$ group, if any are present, is independently an alkyl, aralkyl, or aryl group, and is attached to the silicon atom (noting that no $R^a$ group will be present when n is 0). Each X is a leaving group covalently bonded to the silicon atom and is independently alkoxy or acyloxy, and n is 0, 1, or 2.

In some embodiments, Y is a divalent alkylene group. A typical alkylene can be up to 20, up to 16, 12, 10, 8, 7, 6, 5, 4, or even up to 3 carbons, or even 2 carbons. In some embodiments, Y is a divalent group comprising an alkylene of 3 to 6 carbons. In a preferred embodiment, Y is a divalent group having 3 carbons (i.e., propyl), as shown, for example in the preferred linker compound of Formula 6.

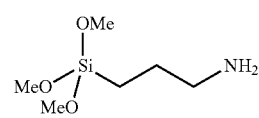

Formula 6

In some embodiments, a first step of a method of making a guanidine-functionalized metal silicate particle is shown in Reaction Scheme 1, reacting a compound of Formula 5 with an O-alkylisourea (R' can be methyl or other lower alkyl, including anywhere from 2 to 10 carbons). The reaction can be carried out in a suitable solvent (e.g., methanol or ethanol).

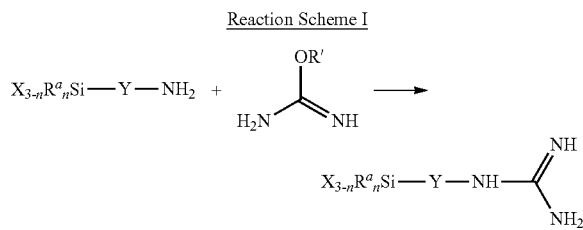

In a more specific embodiment of Reaction Scheme I, the compound of Formula 6 is reacted with an O-methylisourea salt, as shown in Reaction Scheme II.

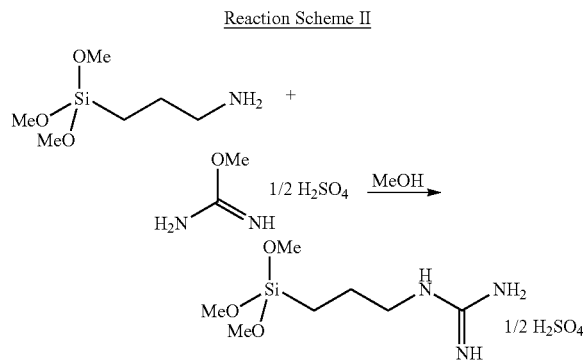

In Reaction Scheme II, O-methylisourea is provided as a hemisulfate, and is reacted with 3-aminopropyltrimethoxysilane (in methanol) to form the guanidine group (noting that the charge state of the guanidine group and of the associated hemisulfate counterion are not shown in Reaction Scheme II).

It will be appreciated that Formula 6 and Reaction Scheme II are representative examples and that any suitable linker molecule can be used (as long as the linker molecule includes, e.g., a primary amine that can be reacted with the O-methylisourea to form a guanidine group), within the overall boundaries prescribed herein. For example, the linker molecule can comprise any desired number of any suitable reactive groups (e.g., ethoxy, methoxy, acetoxy) on the silicon atom (noting that if multiple reactive groups are present they do not have to be identical; further noting that if less than three such reactive groups are used, other (e.g., $R^a$) groups can be present, e.g. as shown in the general representation of Formula 4, and still further noting that if multiple $R^a$ groups are present they do not have to be identical). In a specific example, 3-aminopropyltriethoxysilane may be used as the linker molecule rather than the 3-aminopropyltrimethoxysilane of Formula 6 and included in Reaction Scheme II.

In some embodiments, Y is a divalent group comprising an alkylene, and the divalent group can further optionally comprise other groups, including an arylene, oxy, —NH—, or a combination thereof. In some specific embodiments, the divalent Y group of the linker molecule may comprise a secondary amine. In a particular example of this type, the linker molecule may be e.g. N-(2-aminoethyl)-3-aminopropyltrimethoxysilane (available under the trade designation "SIA0591.0" from Gelest, Inc., Tullytown, Pa.). Other potentially useful linker molecules may include e.g. (aminoethylaminomethyl) phenethyltrimethoxysilane ("SIA0588.0", Gelest), N-(2-aminoethyl)-3-aminopropylmethyldimethoxysilane ("SIA0589.0", Gelest), N-(6-aminohexyl) aminopropyltrimethoxysilane ("SIA0594.0", Gelest), N-(2-aminoethyl)-11-aminoundecyl-trimethoxysilane ("SIA05951.0", Gelest), N-3 [(amino(polypropylenoxy)] aminopropyltrimethoxysilane ("SIA0599.4", Gelest), 3-aminopropylmethyldiethoxysilane ("SIA0605.0", Gelest), 3-aminopropyltriethoxysilane ("SIA0610.0", Gelest), and (3-trimethoxysilylpropyl)diethylene-triamine ("SIT8398.0", Gelest). Mixtures of any of the herein-mentioned linker molecules may be used if desired.

In a second step of this method, at least one of the Si-bonded X groups of the linker molecule (with Si atoms comprising one or more such reactive alkoxy or acyloxy groups being well known by the term silane coupling agents) is reacted with a hydroxyl group of a suitable particle to form a covalent bond between the linker molecule and the particle. (It is emphasized that the terminology of "first" and "second" steps is used purely for convenience of description and that the steps can be performed in any desired order). For example, any or all of the three trimethoxy reactive groups of the linker molecule in Reaction Scheme II may react with surface hydroxyl groups of the particle. In some embodiments, and as mentioned above, the addition of water in the second step of this method has been observed to result in higher surface nitrogen values as measured by XPS (see Example section). The amount of water added can be in a range from 0 to 5 equivalents ("eq") of water relative to the amount of linker molecule ("equivalents" here refers to "molar equivalents", defined as 1 mole of water for each 1 mole of linker molecule), which can include up to 1 eq, or up to 2 eq, up to 1 eq, up to 0.5 eq, up to 0.25 eq, or even any value in between 0 eq and 5 eq of water, relative the amount of linker molecule.

In one embodiment, the net result of these two steps is summarized in exemplary embodiment in Formula 7 (the circle in Formula 7 represents a metal silicate particle):

Formula 7

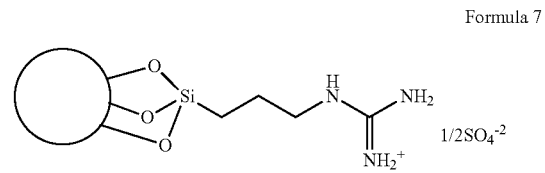

The specific exemplary representation of Formula 7 shows the thus-produced guanidine group in a positively charged (e.g., protonated) condition with a negatively charged hemisulfate counterion associated therewith. It will be understood that a guanidine-functionalized particle may be produced in such condition by the above method, but that the charge state of the guanidine group, the presence, identity and/or charge state of a counterion, etc., may be affected thereafter by the environment into which the guanidine-functionalized particle is placed, as discussed above.

The general methods-of-making described above, and materials used therein, may be tailored as desired for particular purposes. Thus, in some embodiments, each thus-formed guanidine-containing ligand on the particle may only have a single guanidine group (rather than there being e.g. two, three or more guanidine groups on a given guanidine-containing ligand). In some embodiments, the thus-formed guanidine-comprising ligands may be the only ligands on the particle (rather than there being additional ligands, e.g. silane-coupled ligands, on the particle, which additional ligands do not comprise a guanidine group). In some embodiments, a substantial amount (e.g., an amount readily detectable by surface analysis) of residual hydroxyls are present on the surface of the particle even after the attachment of the linker molecules to some of the hydroxyls of the particle to form ligands thereon (e.g., rather than the residual hydroxyls being endcapped). In some embodiments, the methods disclosed herein do not include a step of equilibrating the particle in an atmosphere having a defined relatively humidity (e.g., of less than 40%) prior to the reacting of the linker molecule with a surface hydroxyl group of the particle.

While the method outlined in Reaction Scheme II uses an O-methylisourea, it will be appreciated that other starting materials might be used to make a guanidine-functionalized linker of the general structure of Formula 1. Such starting materials might include e.g. O-alkylisourea salts such as O-methylisourea sulfate, O-methylisourea hydrogen sulfate, O-methylisourea acetate, O-ethylisourea hydrogen sulfate, and O-ethylisourea hydrochloride. Beyond these materials, other starting materials that might be used to make a guanidine-functionalized linker of the general structure of Formula 1 might include e.g. cyanamide, chloroformamidine hydrochloride; 1-amidino-1,2,4-triazole hydrochloride; 3,5-dimethylpyrazole-1-carboxamidine nitrate; pyrazole-1-carboxamidine hydrochloride; N-amidinopyrazole-1-carboxamidine hydrochloride. It will be appreciated that some of these starting materials may produce a guanidine-containing linker in which the guanidine group is in a specific charge state (e.g., is a free base or is positively charged) and/or has a specific counterion associated therewith. It will be understood that such a guanidine group may be placed into a specific charge state, may have its associated counterion exchanged for some other counterion, and so on, based on the disclosures herein.

Laminated articles of the present disclosure include those that comprise (a) a porous fibrous nonwoven matrix, (b) a plurality of the above-described guanidine-functionalized metal silicate particles, the particles being enmeshed in the porous fibrous nonwoven matrix, a first substrate, and a second substrate sealed to the first substrate along at least a portion of a perimeter of the first substrate. The particle-containing porous fibrous nonwoven matrix is disposed between the first substrate and the second substrate. Preferably, the guanidine-functionalized metal silicate particles are guanidine-functionalized magnesium silicate particles. Such porous fibrous nonwoven matrices can be prepared by essentially any process that is capable of providing a fibrous nonwoven matrix (that is, a web or medium, other than a woven or knitted fabric, comprising interlaid fibers) having the particles enmeshed therein. Useful processes include meltblowing, spunbonding, and other air laying techniques; carding; wet laying; and the like; and combinations thereof (preferably, air laying, wet laying, and combinations thereof; more preferably, wet laying).

Fibers that are suitable for use in preparing the porous fibrous nonwoven matrix of a laminated article of the present disclosure include pulpable fibers. Preferred pulpable fibers are those that are stable to radiation and/or to a variety of solvents. Useful fibers include polymeric fibers, inorganic fibers, and combinations thereof (preferably, polymeric fibers and combinations thereof). Preferably, at least some of the fibers that are utilized exhibit a degree of hydrophilicity.

Suitable polymeric fibers include those made from natural (animal or vegetable) and/or synthetic polymers, including thermoplastic and solvent-dispersible polymers. Useful polymers include wool; silk; cellulosic polymers (for example, cellulose, cellulose derivatives, and the like); fluorinated polymers (for example, poly(vinyl fluoride), poly (vinylidene fluoride), copolymers of vinylidene fluoride such as poly(vinylidene fluoride-co-hexafluoropropylene), copolymers of chlorotrifluoroethylene such as poly(ethylene-co-chlorotrifluoroethylene), and the like); chlorinated polymers; polyolefins (for example, poly(ethylene), poly (propylene), poly(l-butene), copolymers of ethylene and propylene, alpha olefin copolymers such as copolymers of ethylene or propylene with 1-butene, 1-hexene, 1-octene, and 1-decene, poly(ethylene-co-1-butene), poly(ethylene-co-1-butene-co-1-hexene), and the like); poly(isoprenes); poly(butadienes); polyamides (for example, nylon 6; nylon 6,6; nylon 6,12; poly(iminoadipoyliminohexamethylene); poly(iminoadipoyliminodecamethylene); polycaprolactam; and the like); polyimides (for example, poly(pyromellitimide) and the like); polyethers; poly(ether sulfones) (for example, poly(diphenylether sulfone), poly(diphenylsulfone-co-diphenylene oxide sulfone), and the like); poly (sulfones); poly(vinyl acetates); copolymers of vinyl acetate (for example, poly(ethylene-co-vinyl acetate), copolymers in which at least some of the acetate groups have been hydrolyzed to provide various poly(vinyl alcohols) including poly(ethylene-co-vinyl alcohol), and the like); poly (phosphazenes); poly(vinyl esters); poly(vinyl ethers); poly (vinyl alcohols); polyaramids (for example, para-aramids such as poly(paraphenylene terephthalamide) and fibers sold under the trade designation "KEVLAR" by DuPont Co., Wilmington, Del., pulps of which are commercially available in various grades based on the length of the fibers that make up the pulp such as, for example, "KEVLAR 1F306" and "KEVLAR 1F694", both of which include aramid fibers that are at least 4 mm in length; and the like); poly (carbonates); and the like; and combinations thereof. Preferred polymeric fibers include polyamides, polyolefins, polysulfones, and combinations thereof (more preferably, polyamides, polyolefins, and combinations thereof; most preferably, nylons, poly(ethylene), and combinations thereof).

Suitable inorganic fibers include those that comprise at least one inorganic material selected from glasses, ceramics, and combinations thereof. Useful inorganic fibers include fiberglasses (for example, E-glass, S-glass, and the like), ceramic fibers (for example, fibers made of metal oxides (such as alumina), silicon carbide, boron nitride, boron carbide, and the like), and the like, and combinations thereof. Useful ceramic fibers can be at least partially crystalline (exhibiting a discernible X-ray powder diffraction pattern or containing both crystalline and amorphous (glass) phases). Preferred inorganic fibers include fiberglasses and combinations thereof.

The fibers used to form the porous fibrous nonwoven matrix can be of a length and diameter that can provide a matrix having sufficient structural integrity and sufficient porosity for a particular application (for example, for a particular type of sample matrix). For example, lengths of at least about 0.5 mm, 1 mm, 2 mm, 3 mm, 4 mm, 6 mm, 8 mm, 10 mm, 12 mm, 15 mm, 20 mm, 25 mm, or even 30 mm (and combinations thereof), and diameters of at least about 10 micrometers, 20 micrometers, 40 micrometers, or even 60 micrometers (and combinations thereof) can be useful. Preferred fiber lengths and diameters will vary, depending upon factors including the nature of the fiber and the type of application. For example, fibrillated poly(ethylene) can be useful in lengths of about 1 mm to about 3 mm, and non-fibrillated nylon can be useful in lengths of about 5 mm to about 12.7 mm, for a variety of sample matrices.

To facilitate entrapment of the particles and/or to ensure a high surface area matrix, the fibers used to form the porous fibrous nonwoven matrix preferably comprise at least one fibrillated fiber (for example, in the form of a main fiber surrounded by many smaller attached fibrils). The main fiber generally can have a length in the range of about 0.5 mm to about 4 mm and a diameter of about 1 micrometer to about 20 micrometers. The fibrils typically can have a submicrometer diameter.

The porous fibrous nonwoven matrix can comprise two, three, four, or even more different types of fibers. For example, a nylon fiber can be added for strength and integrity, while fibrillated polyethylene can be added for entrapment of the particulates. If fibrillated and non-fibrillated fibers are used, generally the weight ratio of fibrillated fibers to non-fibrillated fibers can be at least about 1:2, 1:1, 2:1, 3:1, 5:1, or even 8:1. Regardless of the type(s) of fibers chosen, the amount of fiber in the resulting porous fibrous nonwoven matrix (in dry form) is preferably at least about 10, 12, 12.5, 14, 15, 18, 20, or even 22 percent by weight up to about 20, 30, 40, 50, 60, 70, or even 80 percent by weight (based upon the total weight of all components of the porous fibrous nonwoven matrix).

Preferably, the porous fibrous nonwoven matrix further comprises at least one polymeric binder. Suitable polymeric binders include natural and synthetic polymeric materials that are relatively inert (exhibiting little or no chemical interaction with either the fibers or the guanidine-functionalized metal silicate particles). Useful polymeric binders include polymeric resins (for example, in the form of powders and latexes), polymeric binder fibers, and the like, and combinations thereof. For some applications, polymeric binders can include polymeric binder fibers and combinations thereof. For other applications, polymeric resins and combinations thereof can be preferred polymeric binders.

Suitable polymeric resins for the polymeric binder can include, but are not limited to, natural rubbers, neoprene, styrene-butadiene copolymers, acrylate resins, polyvinyl chloride, polyvinyl acetate, ultra-high molecular weight polyethylene (UHMWPE), and the like, and combinations thereof. Preferred polymeric resins include acrylate resins and combinations thereof. Suitable polymeric binder fibers can include adhesive-only type fibers (for example, "KODEL 43UD" fibers, available from Eastman Chemical Products, Kingsport, Tenn.), bicomponent fibers (for example, side-by-side forms such as "CHISSO ES" polyolefin thermally bonded bicomponent fibers, available from Chisso Corporation, Osaka, Japan; sheath-core forms such as "MELTY FIBER TYPE 4080" bicomponent fibers having a polyester core and a polyethylene sheath, available from Unitika Ltd., Osaka, Japan; and the like), and the like, and combinations thereof. Preferred polymeric binder fibers include bicomponent fibers and combinations thereof (more preferably, sheath-core bicomponent fibers and combinations thereof).

Regardless of the type of polymeric binder used, the amount of binder in the resulting porous fibrous nonwoven matrix (in dry form) can be from about 3 weight percent to about 7 weight percent including about 5 weight percent, based upon the total weight of all components of the porous fibrous nonwoven matrix. Such amounts of polymeric binder generally can provide the porous fibrous nonwoven matrix with sufficient integrity for use in many applications, while not significantly coating the particles. Surprisingly, the amount of polymeric binder in the nonwoven matrix can be less than about 5, 4, 3, 2, or even 1 percent by weight, relative to the weight of the fibers in the nonwoven matrix.

Substrates that are suitable for laminated articles of the present disclosure include a spunbond polypropylene, a spunbond blend of polyamide and polyester, a spunbond polyamide, a spunbond polyethylene, a spunbond polyester, a spunbond polybutylene terephthalate (PBT), a spunbond polypropylene, a melt-blown web, a staple web, and most preferably a spunbond polypropylene or a spunbond blend of polyamide and polyester. Preferably, each of the first substrate and the second substrate are selected from materials that shed few or no fibers, such that the turbidity of a fluid sample passed through the laminated article is not detectably increased as compared to the turbidity of the fluid sample prior to being passed through the laminated article, or passes the Turbidity Test described below. The first substrate and the second substrate are independently selected from suitable materials, but often include the same material. It is emphasized that the terminology of "first" and "second" substrates is used purely for convenience of description; in certain embodiments, the first substrate and the second substrate are portions of a single continuous substrate, whereas in alternate embodiments the first substrate and the second substrate are individual, separate, substrates. One example of the first substrate and the second substrate being portions of a single continuous substrate, for instance, is a substrate folded in half wherein one half provides the first substrate while the other half provides the second substrate. In certain embodiments, more than two substrates are employed; for example, a third substrate is optionally laminated to the first substrate and/or to the second substrate, to provide at least one additional substrate layer. Likewise, a fourth substrate, a fifth substrate, etc., may be laminated to the first substrate and/or to the second substrate. In such embodiments, the third substrate (or fourth substrate, or fifth substrate, etc.) is the same as or different from the substrate to which it is laminated. In an embodiment, the third substrate has a different basis weight than the first substrate to assist in preventing an increase in turbidity in a fluid sample when passed through the laminated article; for instance the first substrate (adjacent to the porous fibrous nonwoven matrix) optionally has a smaller basis weight than the third substrate (laminated to the first substrate opposite of the porous fibrous nonwoven matrix).

To allow flow of a liquid (e.g., a fluid sample) through the thickness of the laminated article, each of the first substrate and the second substrate is liquid permeable. In many applications, liquids comprising water (e.g., aqueous solutions) will be passed through the laminated article, thus preferably at least one of the first substrate and the second substrate comprise a hydrophilized substrate to improve wettability and penetration of the liquid through one or both substrates. Hydrophilization is well known to the skilled practitioner, and may be performed using plasma treatment, for instance (see, e.g., U.S. Pat. No. 4,772,488).

Characteristics of spunbond materials typically correlated to porosity include the basis weight of a unit area of the material and the diameter of the individual fibers of which the spunbond materials are composed. Suitable substrates for laminated articles according to the present disclosure include one or more spunbond materials comprising a gram per square meter basis weight (gsm) of at least about 10, 25, 40, 55, 60, or even 65 gsm up to about 75, 80, 90, 100, 140, 180, or even 200 gsm. For example, in certain aspects, the first substrate and the second substrate independently include a spunbond material comprising a gsm of 10 to 200 gsm, preferably 55 to 100 gsm, and most preferably 60 to 100 gsm, inclusive. In certain aspects, the first substrate and the second substrate independently comprise a spunbond material comprising a fiber diameter of at least about 10 micrometers (μm), 11, 12, 13, 14, or even 15 μm up to about 17, 18, 19, 20, 22, 24, 26, 28, or even 30 μm. For example, in certain aspects, the first substrate and the second substrate independently comprise a spunbond material comprising a fiber diameter of 10 to 30 μm, and preferably 10 to 18 μm, 12 to 20 μm, or 14 to 22 μm, inclusive.

Depending on the application, the laminated article according to the present disclosure further comprises additional particles. For instance, in an embodiment a plurality of guanidine-functionalized silica gel particles, a plurality of diatomaceous particles, or a combination thereof is also enmeshed within the porous fibrous nonwoven matrix with the plurality of guanidine-functionalized metal silicate particles. Suitable guanidine-functionalized silica gel particles are disclosed in U.S. Provisional Application No. 61/733,156, filed Dec. 4, 2012 (Griesgraber et al.; 3M Innovative Properties Company), the descriptions of the particles and methods of their preparation being incorporated herein by reference. Suitable diatomaceous earth particles are disclosed in U.S. Application Publication No. US 2010/0209961 published on Aug. 19, 2010 (Kshirsagar et al.; 3M Innovative Properties Company), the descriptions of the particles and methods of modifying their surfaces being incorporated herein by reference.

Laminated articles of the present disclosure include a seal to secure the first substrate to the second substrate. In particular, the second substrate is sealed to the first substrate along at least a portion of the perimeter of the substrate. As used herein, the term "perimeter" means the border or outer boundary of a substrate, including all of the area within about 10% of the distance of the furthest edge of the border or outer boundary inward towards the center of the substrate. For instance, if a substrate comprises a circular shape having a radius of 10 centimeters (cm), the perimeter includes any of the area from the outer edge to 1 cm in from the outer edge toward the center of the circular shape. Alternatively, if a substrate comprises a rectangle (e.g., polygon) shape having a length of 40 cm and a height of 20 cm, the perimeter includes any of the area from the outer edges of the short ends to 4 cm in towards the center point of the rectangle and from the outer edges of the long ends to 2 cm in towards the center point of the rectangle. Typically, the second substrate is sealed to the first substrate along at least about 50%, or 60%, or 75% or 85%, or even 90% of the perimeter of the first substrate up to about 95% or even 100% of the of the perimeter of the first substrate. In addition to the sealing along at least a portion of the perimeter of the first substrate, point bonding (or pin bonding) of discreet points inward of the perimeter of the first substrate is optionally also employed. An advantage of performing point bonding is providing further stability of the porous fibrous nonwoven matrix material remaining where it was originally disposed between the first and second substrates.

Sealing of the first substrate to the second substrate may be accomplished by various suitable methods known in the art, including for example and without limitation, ultrasonic sealing, heat sealing, adhesive sealing, stitching, or a combination thereof. Ultrasonic sealing may be a preferred method, and is typically performed at an energy setting of at least about 150 joules (J), or 175 J, or 200 J, or even 225 J, up to about 200 J, 225 J, or even 250 J, for example 150 J to 250 J, inclusive. In certain embodiments, the ultrasonic sealing simultaneously seals and cuts the laminated article in a single step, eliminating the need for individually separating the laminated article from substrate and/or porous fibrous nonwoven matrix material.

Laminated articles of the present disclosure can be prepared by a process comprising (a) providing a plurality of the above-described fibers; (b) providing a plurality of the above-described guanidine-functionalized metal silicate particles; (c) mixing the plurality of guanidine-functionalized metal silicate particles and the plurality of fibers together to form a porous fibrous nonwoven matrix having the guanidine-functionalized metal silicate particles enmeshed within the porous fibrous nonwoven matrix; (d) providing the above-described first substrate; (e) providing the above-described second substrate; (f) disposing the porous fibrous nonwoven matrix having the guanidine-functionalized metal silicate particles between the first substrate and the second substrate; and (g) sealing the second substrate to the first substrate along at least a portion of a perimeter of the first substrate (as described above).

Mixing the plurality of guanidine-functionalized metal silicate particles and the plurality of fibers together to form a porous fibrous nonwoven matrix having the guanidine-functionalized metal silicate particles enmeshed within the porous fibrous nonwoven matrix can be carried out by essentially any process that is capable of providing a fibrous nonwoven matrix (that is, a web or medium, other than a woven or knitted fabric, comprising interlaid fibers) having the guanidine-functionalized metal silicate particles enmeshed therein. Useful processes include meltblowing, spunbonding, and other air laying techniques; carding; wet laying; and the like; and combinations thereof (preferably, air laying, wet laying, and combinations thereof; more preferably, wet laying).

Preferably, the forming of the porous fibrous nonwoven matrix is carried out by using a wet laying or "wetlaid" process comprising (a) forming a dispersion comprising the plurality of fibers, the plurality of particles (which can be added and dispersed along with the other components prior to carrying out other process steps or, if desired, can be added and dispersed later in the process but generally prior to removal of dispersing liquid), and at least one polymeric binder in at least one dispersing liquid (preferably, water); (b) at least partially depositing the polymeric binder onto at least a portion of the fibers; and (c) removing the dispersing liquid from the dispersion. In such a process, the fibers can be dispersed in the dispersing liquid to form a slurry. If desired, the fibers can comprise additives or chemical groups or moieties to assist in their dispersion. For example, polyolefin-based fibers can comprise maleic anhydride or succinic anhydride functionality, or, during the melt-processing of polyethylene fibers, a suitable surfactant can be added.

Deposition of the polymeric binder onto the fibers can be carried out either before or after the dispersing liquid removal or dewatering step, depending upon the nature of the polymeric binder. For example, when a polymeric latex is used as the polymeric binder, the polymeric latex can be precipitated onto the fibers before or after particle addition and prior to dewatering. After the dewatering, heat can be applied to finish the dewatering and to set the resulting deposited latex. When polymeric binder fibers are used as the polymeric binder, dewatering can generally be carried out first, followed by heating to finish the dewatering and to melt the polymeric binder fibers (and thereby deposit polymeric binder on the fibers). Optionally, mixing the polymeric binder with the fibers includes forming a nonwoven wetlaid scaffold. In certain embodiments, at least one polymeric binder is mixed together with the plurality of guanidine-functionalized metal silicate particles and the plurality of fibers.

One or more adjuvants or additives can be used in preparing the porous fibrous nonwoven matrix. Useful adjuvants include process aids (for example, precipitation agents such as sodium aluminate and aluminum sulfate, which can aid in precipitating the polymeric binder onto the fibers), materials that can enhance the overall performance of the resulting porous fibrous nonwoven matrix, and the like. When used, the amounts of such adjuvants can range from more than zero up to about 2 weight percent (preferably, up to about 0.5 weight percent; based upon the total weight of the components of the porous fibrous nonwoven matrix), although their amounts are preferably kept as low as possible so as to maximize the amount of particles that can be included.

In a preferred wetlaid process, the fibers (for example, chopped fibers) can be blended in a container in the presence of the dispersing liquid (for example, water, a water-miscible organic solvent such as an alcohol, or a combination thereof). The amount of shear used to blend the resulting mixture has not been found to affect the ultimate properties of the resulting porous fibrous nonwoven matrix, although the amount of shear introduced during blending is preferably relatively high. Thereafter, the particles, the polymeric binder, and an excess of a precipitation agent (for example, a pH adjusting agent such as alum) can be added to the container.

When the preferred wetlaid process is carried out by using hand-sheet methods known in the art, the order of addition of the three ingredients to the fiber dispersion has not been found to significantly affect the ultimate performance of the laminated article. In some embodiments, addition of the polymeric binder after addition of the particles, however, can provide a porous fibrous nonwoven matrix exhibiting somewhat greater adhesion of the particles to the fibers. When the preferred wetlaid process is carried out by using a continuous method, the three ingredients preferably are added in the listed order. (The following description is based on a hand-sheet method, although those skilled in the art can readily recognize how to adapt such a method to provide for a continuous process.)

After the particles and the polymeric binder are added to the fiber-liquid slurry, the resulting mixture can be poured into a mold, the bottom of which can be covered by a screen. The dispersing liquid (preferably, water) can be allowed to drain from the mixture (in the form of a wet sheet) through the screen. After sufficient liquid has drained from the sheet, the wet sheet generally can be removed from the mold and dried by pressing, heating, or a combination of the two. Generally pressures of about 300 kPa to about 600 kPa and temperatures of about 100° C. to about 200° C. (preferably, about 100° C. to about 150° C.) can be used in these drying processes. When polymeric binder fibers are used as the polymeric binder in the preferred wetlaid process, no precipitation agent is needed, and the applied heat can be used to melt the polymeric binder fibers.

The resulting dry sheet can have an average thickness of at least about 0.2, 0.5, 0.8, 1, 2, 4, or even 5 mm up to about 5, 8, 10, 15, or even 20 mm. Up to about 100 percent of the dispersing liquid can be removed (preferably, up to about 90 percent by weight). Calendering can be used to provide additional pressing or fusing, if desired.

As mentioned above, the guanidine-functionalized metal silicate particles can be microparticles. The microparticles can be entrapped in the porous fibrous nonwoven matrix through either chemical interactions (for example, chemical bonding) or physical interactions (for example, adsorption or mechanical entrapment), depending upon the nature of the fibers that are utilized. Preferred embodiments of porous fibrous nonwoven matrices of the present disclosure include those comprising at least one fibrillated fiber that can effect mechanical entrapment of the guanidine-functionalized metal silicate particles.

Since the capacity and efficiency of a laminated article of the present disclosure can vary according to the amount of guanidine-functionalized metal silicate particles contained therein, relatively high particle loadings generally can be desirable. The particles are entrapped (e.g., enmeshed) in the porous fibrous nonwoven matrix and preferably distributed within it (more preferably, the particles are distributed essentially uniformly throughout the matrix). In some embodiments, the amount of particles in the porous fibrous nonwoven matrix preferably can be at least about 5, 10, 15, 20, 25, 30 or even 40 weight percent by dry weight (based upon the total weight of all components of the porous fibrous nonwoven matrix containing the particles). In some embodiments, the amount of particles in the porous fibrous nonwoven matrix preferably can be up to about 20, 25, 30, 40, 50, 60, 70, 80, or even 90 weight percent by dry weight (based upon the total weight of all components of the porous fibrous nonwoven matrix). In some embodiments, the amount of particles in the porous fibrous nonwoven matrix can be in a range from 5 to 90 weight percent, from 5 to 50 weight percent, or even from 20 to 70 weight percent by dry weight, (based upon the total weight of all components of the porous fibrous nonwoven matrix), or any combination of the lower and upper limits, including any value between these lower and upper limits.

Generally the average pore size of the sheet material can be in the range of about 0.1 to about 10 micrometers, as measured by scanning electron microscopy ("SEM"). Void volumes in the range of about 20 to about 80 volume percent can be useful (preferably, about 40 to about 60 volume percent). The porosity of the sheet materials can be modified (increased) by including fibers of larger diameter or stiffness in the fiber mixture.

The sheet material can be flexible (for example, able to be rolled around a 0.75 inch (about 2 cm) diameter core). This flexibility can enable the sheet material to be pleated or rolled. The porous sheet has an open pore structure that tends to provide minimal resistance to the passage of samples (e.g., a fluid stream such as a liquid sample). Because of this minimal resistance, relatively high volumes of liquid can be relatively quickly passed through it without generating a relatively high back pressure.

The uncalendered sheet material can be cut to a desired size, disposed between the first substrate and the second substrate, and sealed to form a laminated article that is optionally used to carry out the microorganism removal process of the present disclosure. In some embodiment a single layer of sheet material can be effective in carrying out the method of the present disclosure for removing microorganism. Multiple layers can be used between the first and second substrates, if desired, to provide greater removal capacity.

A significant advantage of the porous fibrous nonwoven matrix of the laminated article is that very small guanidine-functionalized metal silicate particle sizes (10 micrometers or smaller) and/or guanidine-functionalized metal silicate particle with a relatively broad size distribution can be employed. This allows for excellent one-pass kinetics, due to increased surface area/mass ratios. Because of the relatively low pressure drops, a minimal driving force (such as gravity or a vacuum) can be used to pull a sample through the laminated article, even when small guanidine-functionalized metal silicate particle sizes are employed.

A method of removing microorganisms from a fluid sample (e.g., an aqueous sample) is provided, using laminated articles of the present disclosure. The method includes (a) providing laminated article as described above; (b) providing a fluid sample containing at least one microorganism strain; and (c) contacting the fluid sample with the laminated article such that at least a portion of the at least one microorganism strain is removed from the fluid sample. Preferably, the contacting includes passing the fluid sample at least once through the laminated article.

The fluid sample can be provided from a variety of different types of samples, including, but not limited to, medical, environmental, food, feed, clinical, and laboratory samples, and combinations thereof. Medical or veterinary samples can include, for example, cells, tissues, or fluids from a biological source (for example, a human or an animal) that are to be assayed for clinical diagnosis. Environmental samples can be, for example, from a medical or veterinary facility, an industrial facility, soil, a water source, a food preparation area (food contact and non-contact areas), or a laboratory. Drinking water from a water source is a preferred fluid sample, as drinking water can have microorganisms removed at the tap immediately prior to use according to methods of the present disclosure. Food processing, handling, and preparation area samples are also preferred, as these are often of particular concern in regard to food supply contamination by bacterial pathogens.

Fluid samples obtained in the form of a liquid or in the form of a dispersion or suspension of solid in liquid can be used directly, or can be concentrated (for example, by centrifugation) or diluted (for example, by the addition of a buffer (pH-controlled) solution). Samples in the form of a solid or a semi-solid can be extracted, if desired, by a method such as, for example, washing or rinsing with, or suspending or dispersing in, a fluid medium (for example, a buffer solution). Samples can be taken from surfaces (for example, by swabbing or rinsing). Preferably, the sample is at least a fluid (for example, a liquid, a gas, or a dispersion or suspension of solid or liquid in liquid or gas).

Examples of samples that can be used include beverages (for example, juices or carbonated beverages), water (including potable water), biological fluids, and the like. Preferred samples include beverages, water, and combinations thereof (with water being most preferred).

Sample volume can vary, depending upon the particular application. For example, for a diagnostic or research application, the volume of the sample can typically be in the microliter range (for example, 10 microliters or greater). When a filtering process is used for potable water safety testing, the volume of the sample can typically be in the milliliter to liter range (for example, 100 milliliters to 3 liters). In industrial or residential applications, the volume can be tens of thousands of liters.

The process of the present disclosure can be carried out by any of various known or hereafter-developed methods of providing contact between two materials. For example, the laminated article can be added to the sample, or the sample can be added to the laminated article. The laminated article can be immersed in a sample, a sample can be poured onto the laminated article, a sample can be poured into a tube or well containing the laminated article, or, preferably, a sample can be passed over or through (preferably, through) the laminated article (or vice versa). Preferably, the contacting is carried out in a manner such that the sample passes through the first substrate, at least one pore of the porous fibrous nonwoven matrix (preferably, through at least one through pore), and the second substrate.

The laminated article and the sample can be combined (using any order of addition) in any of a variety of containers or holders (optionally, a capped, closed, or sealed container; preferably, a column, a syringe barrel, or another holder designed to contain the laminated article with essentially no sample leakage). Suitable containers for use in carrying out the process of the present disclosure will be determined by the particular sample and can vary widely in size and nature. For example, the container can be small, such as a 10 microliter container (for example, a test tube or syringe) or larger, such as a 100 milliliter to 3 liter container (for example, an Erlenmeyer flask or an annular cylindrical container).

The container, the laminated article, and any other apparatus or additives that contact the sample directly can be sterilized (for example, by controlled heat, ethylene oxide gas, or radiation) prior to use, in order to reduce or prevent any contamination of the sample that might cause detection errors. The amount of guanidine-functionalized metal silicate particle in the porous fibrous nonwoven matrix that is sufficient to provide successful removal of microorganisms of a particular sample will vary and can be readily determined by one skilled in the art.

In an embodiment of the present disclosure, a filtration device is includes a container having inlet and outlet ports for liquid passage, and a laminated article of the present disclosure contained within the container.

Contacting can be carried out for a desired period (for example, for sample volumes of several liters or for processes involving multiple passes through the laminated article, up to about 60 minutes of contacting can be useful; preferably, about 15 seconds to about 10 minutes or longer; more preferably, about 15 seconds to about 5 minutes; most preferably, about 15 seconds to about 2 minutes).

Preferably, contacting can be effected by passing a sample at least once (preferably, only once) through the laminated article (for example, by gravity, by vacuum, or by pumping). Essentially any type of pump (for example, a peristaltic pump) or other equipment for establishing a pressure differential across a sample of the laminated article contained in a suitable container having inlet and outlet ports for liquid passage (for example, a syringe or plunger) can be utilized. Useful flow rates will vary, depending upon such factors as the nature of the sample matrix and the particular application. Advantageously, the laminated articles of the present disclosure require only a very low pressure differential across the laminated article to effectively pass a fluid sample through the laminated article. This characteristic is particularly beneficial in environments, for instance, where a water supply has a low pressure flow at the tap (e.g., locations in which water is stored on rooftop tanks of buildings), and/or when no or low power pumps are available for transporting a fluid sample. In an embodiment of the present disclosure, the contacting comprises passing the fluid sample through the laminated article at a pressure of 4.0 pounds per square inch (psi) (27.58 kilopascals (kPa)) or less, or 3.0 psi (20.68 kPa), or 2.0 psi (13.79 kPa), or 1.0 psi (6.9 kPa), or 0.9 psi (6.21 kPa), or 0.8 psi (5.52 kPa), or 0.7 psi (4.83 kPa), or 0.6 psi (4.14 kPa), or even 0.5 psi (3.45 kPa) or less, and at a pressure of at least 0.4 psi (2.76 kPa), or at least 0.5 psi (3.45 kPa).

For example, sample flow rates through the laminated article of up to about 100 milliliters per minute or more can be effective. Preferably, for samples such as beverages and water, flow rates of about 10-20 milliliters per minute can be utilized. For pre-filtered or otherwise clarified food samples, flow rates of about 6 milliliters per minute (1.5 milliliters per 15 seconds) can be useful. Longer contact times and slower flow rates can be useful for more complex sample matrices such as ground beef or turkey.

A preferred contacting method includes such passing of a sample through the laminated article (for example, by gravity or by pumping). If desired, one or more additives (for example, lysis reagents, bioluminescence assay reagents, nucleic acid capture reagents (for example, magnetic beads), microbial growth media, buffers (for example, to moisten a solid sample), microbial staining reagents, washing buffers (for example, to wash away unbound material), elution agents (for example, serum albumin), surfactants (for example, "TRITON X-100" nonionic surfactant available from Union Carbide Chemicals and Plastics, Houston, Tex.), adsorption buffers, and the like can be included in a combination of the laminated article and sample after contacting.

Advantageously, the laminated article of the present disclosure sufficiently encapsulates the porous fibrous nonwoven matrix and the first and second substrates maintain their integrity, such that the laminated article provides a turbidity of less than 0.2 nephelometric turbidity units (NTU), or less than 0.15 NTU, or less than 0.10 NTU, according to the Turbidity Test. The Turbidity Test is an indicator of how much (if any) material (e.g., fibers, binder, and/or particles) from the porous fibrous nonwoven matrix and/or the substrates could potentially be shed during use of the laminated article. The Turbidity Test is significant in particular when the fluid sample contacted with the laminated article is intended to be used following the contact, for instance, when the fluid sample is potable water. The Turbidity Test is described in detail in the Examples section below.

The process of the present disclosure can optionally further comprise separating the resulting microorganism-bound laminated article and the sample. Separation can be carried out by numerous methods that are well-known in the art (for example, by pumping, decanting, or siphoning a fluid sample, so as to leave the microorganism-bound laminated article in the container or holder utilized in carrying out the process). It can also be possible to isolate or separate captured microorganisms (target microorganisms or one or more components thereof) from the laminated article after sample contacting (for example, by passing an elution agent or a lysis agent over or through the laminated article). In certain embodiments of the present disclosure, the method of removing microorganisms from a fluid sample reduces the amount of microorganism in the fluid sample by at least a factor of 100, or at least a factor of 1,000, or at least a factor of 10,000, or even at least a factor of 50,000.

The process of the present disclosure can be carried out manually (for example, in a batch-wise manner) or can be automated (for example, to enable continuous or semi-continuous processing).

SELECT EMBODIMENTS OF THE PRESENT DISCLOSURE

Various embodiments are provided that include the following items:

Item 1. A laminated article comprising:
 a) a porous fibrous nonwoven matrix;
 b) a plurality of guanidine-functionalized metal silicate particles enmeshed within the porous fibrous nonwoven matrix, the guanidine-functionalized metal silicate particles comprising:
 a metal silicate particle that is modified with at least one silane having the formula

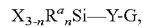

wherein:
  n is 0, 1, or 2;
  each $R^a$, if present, is independently an alkyl, aralkyl, or aryl;
  Y is a divalent group comprising an alkylene having 2 to 20 carbons;
  G is a guanidine group of the formula —NH—C(=NH)—NH$_2$; and
  each X is independently alkoxy or acyloxy;
 c) a first substrate; and
 d) a second substrate sealed to the first substrate along at least a portion of a perimeter of the first substrate, wherein the porous fibrous nonwoven matrix is disposed between the first substrate and the second substrate.

Item 2. The laminated article of item 1, wherein the first substrate and the second substrate are independently selected from a spunbond polypropylene, a spunbond polyamide, a spunbond blend of polyamide and polyester, a spunbond polyethylene, a spunbond polyester, a spunbond polybutylene terephthalate, and a spunbond polypropylene.

Item 3. The laminated article of item 1 or item 2, wherein the first substrate and the second substrate are independently selected from a spunbond polypropylene and a spunbond blend of polyamide and polyester.

Item 4. The laminated article of any one of items 1 to 3 wherein the first substrate and the second substrate independently comprise a spunbond material comprising a gram per square meter basis weight (gsm) of 10 to 200 gsm, inclusive.

Item 5. The laminated article of any one of items 1 to 4 wherein the first substrate and the second substrate independently comprise a spunbond material comprising a gram per square meter basis weight (gsm) of 55 to 100 gsm, inclusive.

Item 6. The laminated article of any one of items 1 to 5 wherein the first substrate and the second substrate independently comprise a spunbond material comprising a gram per square meter basis weight (gsm) of 60 to 100 gsm, inclusive.

Item 7. The laminated article of any one of items 1 to 6 wherein the first substrate and the second substrate independently comprise a spunbond material comprising a fiber diameter of 10 to 30 micrometers (μm), inclusive.

Item 8. The laminated article of any one of items 1 to 7 wherein the first substrate and the second substrate independently comprise a spunbond material comprising a fiber diameter of 10 to 18 μm, inclusive.

Item 9. The laminated article of any one of items 1 to 7 wherein the first substrate and the second substrate independently comprise a spunbond material comprising a fiber diameter of 12 to 20 μm, inclusive.

Item 10. The laminated article of any one of items 1 to 7 wherein the first substrate and the second substrate independently comprise a spunbond material comprising a fiber diameter of 14 to 22 μm, inclusive.

Item 11. The laminated article of any one of items 1 to 10, wherein the porous fibrous nonwoven matrix contains the plurality of guanidine-functionalized metal silicate particles in a range of 5 wt. % to 50 wt. % by dry weight, relative to a total dry weight of the porous fibrous nonwoven matrix containing the particles.

Item 12. The laminated article of any one of items 1 to 11 further comprising a plurality of guanidine-functionalized silica gel particles enmeshed within the porous fibrous nonwoven matrix.

Item 13. The laminated article of any one of items 1 to 12 further comprising a plurality of diatomaceous earth particles enmeshed within the porous fibrous nonwoven matrix.

Item 14. The laminated article of any one of items 1 to 13 wherein the first substrate and the second substrate comprise the same material.

Item 15. The laminated article of any one of items 1 to 14 wherein the second substrate is sealed to the first substrate along at least 50% of the perimeter of the first substrate.

Item 16. The laminated article of any one of items 1 to 15 wherein the second substrate is sealed to the first substrate along at least 75% of the perimeter of the first substrate.

Item 17. The laminated article of any one of items 1 to 16 wherein the second substrate is sealed to the first substrate along up to 100% of the perimeter of the first substrate.

Item 18. The laminated article of any one of items 1 to 17 wherein the laminated article provides a turbidity of less than 0.2 nephelometric turbidity units (NTU) according to the Turbidity Test.

Item 19. The laminated article of any one of items 1 to 18 wherein the first substrate comprises a circular shape or a polygon shape.

Item 20. The laminated article of any one of items 1 to 19, wherein the divalent group further comprises an arylene, oxy, —NH—, or a combination thereof.

Item 21. The laminated article of any one of items 1 to 20, wherein the divalent group is alkylene having 3 to 6 carbons.

Item 22. The laminated article of any one of items 1 to 21, wherein the guanidine group is the reaction product of a primary amine and an O-methylisourea salt.

Item 23. The laminated article of any one of items 1 to 22, wherein the metal silicate particle is a magnesium silicate particle.

Item 24. The laminated article of item 23, wherein the magnesium silicate particle is an amorphous spheroidized particle.

Item 25. The laminated article of item 23, wherein the magnesium silicate particle comprises a particle size in a range from 5 to 15 micrometers.

Item 26. The laminated article of any one of items 1 to 25, wherein n is 0 or 1, and wherein the silane forms a covalent bond with a second silane having the formula according to item 1.

Item 27. The laminated article of any one of items 1 to 26, wherein the guanidine-functionalized metal silicate particle has a surface nitrogen content in a range from 1 to 10 atomic percent as measured by XPS.

Item 28. The laminated article of any one of items 1 to 27, wherein at least one of the first substrate and the second substrate comprises a hydrophilized substrate.

Item 29. The laminated article of any one of items 1 to 28, wherein each of the first substrate and the second substrate is liquid permeable.

Item 30. A method of making a laminated article, the method comprising:
a) providing a plurality of fibers;
b) providing a plurality of guanidine-functionalized metal silicate particles;
c) mixing the plurality of guanidine-functionalized metal silicate particles and the plurality of fibers together to form a porous fibrous nonwoven matrix having the guanidine-functionalized metal silicate particles enmeshed within the porous fibrous nonwoven matrix;
d) providing a first substrate;
e) providing a second substrate;
f) disposing the porous fibrous nonwoven matrix having the guanidine-functionalized metal silicate particles between the first substrate and the second substrate; and
g) sealing the second substrate to the first substrate along at least a portion of a perimeter of the first substrate.

Item 31. The method of item 30, wherein the providing a plurality of guanidine-functionalized metal silicate particles comprises:
i) reacting an O-methylisourea salt with a linker comprising the formula

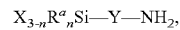

wherein:
n is 0, 1, or 2;
each $R^a$, if present, is independently an alkyl, aralkyl, or aryl;
Y is a divalent group comprising an alkylene having 2 to 20 carbons; and
each X is independently alkoxy or acyloxy;
to form a guanidine-functionalized linker; and
ii) forming a mixture of the guanidine-functionalized linker and metal silicate particles, such that the guanidine-functionalized linker reacts with hydroxyl groups of the metal silicate particles to form covalent bonds between the guanidine-functionalized linker and the metal silicate particles, thereby forming the guanidine-functionalized metal silicate particles.

Item 32. The method of item 31, wherein step (ii) further comprises adding water to the mixture in an amount ranging from 0.1 to 5 equivalents relative to the amount of the guanidine-functionalized linker.

Item 33. The method of item 31 or item 32, wherein the divalent group further comprises an arylene, oxy, —NH—, or a combination thereof.

Item 34. The method of any one of items 31 to 33, wherein the divalent group is alkylene having 3 to 6 carbons.

Item 35. The method of any one of items 31 to 34, wherein the linker is 3-aminopropyltrimethoxysilane.

Item 36. The method of any one of items 31 to 35, wherein the metal silicate particles are magnesium silicate particles.

Item 37. The method of any one of items 31 to 36, wherein the guanidine-functionalized metal silicate particles have a surface nitrogen content in a range from 1 to 10 atomic percent as measured by XPS.

Item 38. The method of any one of items 31 to 37, wherein n is 0 or 1, and wherein the guanidine-functionalized linker forms a covalent bond with a second guanidine-functionalized linker according to step (i) of item 31.

Item 39. The method of any one of items 30 to 38 wherein the second substrate is sealed to the first substrate along at least 50% of the perimeter of the first substrate.

Item 40. The method of any one of items 30 to 39 wherein the second substrate is sealed to the first substrate along at least 75% of the perimeter of the first substrate.

Item 41. The method of any one of items 30 to 40 wherein the second substrate is sealed to the first substrate along up to 100% of the perimeter of the first substrate.

Item 42. The method of any one of items 30 to 41 wherein the laminated article provides a turbidity of less than 0.2 nephelometric turbidity units (NTU) according to the Turbidity Test.

Item 43. The method of any one of items 30 to 42, wherein the first substrate and the second substrate are independently selected from a spunbond polypropylene, a spunbond polyamide, a spunbond blend of polyamide and polyester, a spunbond polyethylene, a spunbond polyester, a spunbond polybutylene terephthalate, and a spunbond polypropylene.

Item 44. The method of any one of items 30 to 43, wherein the first substrate and the second substrate are independently selected from a spunbond polypropylene and a spunbond blend of polyamide and polyester.

Item 45. The method of any one of items 30 to 44 wherein the first substrate and the second substrate independently comprise a spunbond material comprising a gram per square meter basis weight (gsm) of 55 to 100 gsm, inclusive.

Item 46. The method of any one of items 30 to 45 wherein the first substrate and the second substrate independently comprise a spunbond material comprising a gram per square meter basis weight (gsm) of 60 to 100 gsm, inclusive.

Item 47. The method of any one of items 30 to 46 wherein the first substrate and the second substrate independently comprise a spunbond material comprising a fiber diameter of 10 to 30 micrometers (μm), inclusive.

Item 48. The method of any one of items 30 to 47 wherein the first substrate and the second substrate independently comprise a spunbond material comprising a fiber diameter of 10 to 18 μm, inclusive.

Item 49. The method of any one of items 30 to 47 wherein the first substrate and the second substrate independently comprise a spunbond material comprising a fiber diameter of 12 to 20 μm, inclusive.

Item 50. The method of any one of items 30 to 47 wherein the first substrate and the second substrate independently comprise a spunbond material comprising a fiber diameter of 14 to 22 μm, inclusive.

Item 51. The method of any one of items 30 to 50, wherein the porous fibrous nonwoven matrix contains the plurality of guanidine-functionalized metal silicate particles in a range of 5 wt. % to 50 wt. % by dry weight, relative to a total dry weight of the porous fibrous nonwoven matrix containing the particles.

Item 52. The method of any one of items 30 to 51, wherein the sealing is performed using ultrasonic sealing, heat sealing, adhesive sealing, stitching, or a combination thereof.

Item 53. The method of item 52, wherein the sealing is performed using ultrasonic sealing.

Item 54. The method of item 52 or item 53, wherein the ultrasonic sealing comprises an energy setting of 150 joules (J) to 250 J, inclusive.

Item 55. The method of any one of items 30 to 54, wherein fibers in the plurality of fibers comprise polymeric and/or inorganic fibers that can be blended and/or pulped.

Item 56. The method of item 55, wherein the polymeric fibers comprise any of polyethylene, nylon, fiberglass, or combinations thereof.

Item 57. The method of any one of items 30 to 56, wherein at least one of the first substrate and the second substrate comprises a hydrophilized substrate.

Item 58. The method of any one of items 30 to 57, wherein each of the first substrate and the second substrate is liquid permeable.

Item 59. The method of any one of items 30 to 58, further comprising mixing a plurality of guanidine-functionalized silica gel particles together with the guanidine-functionalized metal silicate particles and the plurality of fibers.

Item 60. The method of any one of items 30 to 59, further comprising mixing a plurality of diatomaceous earth particles together with the guanidine-functionalized metal silicate particles and the plurality of fibers.

Item 61. The method of any one of items 30 to 60, further comprising mixing at least one polymeric binder together with the plurality of guanidine-functionalized metal silicate particles and the plurality of fibers.

Item 62. The method of item 61, wherein the mixing includes forming a nonwoven wetlaid scaffold.

Item 63. The method of any one of items 30 to 62, wherein the porous fibrous nonwoven matrix is formed by a wetlaid process.

Item 64. A method of removing microorganisms from a fluid sample, the method comprising:
 a) providing a laminated article according to any one of items 1 to 29;
 b) providing a fluid sample containing at least one microorganism strain; and
 c) contacting the fluid sample with the laminated article such that at least a portion of the at least one microorganism strain is removed from the fluid sample.

Item 65. The method of item 64, further comprising detecting the presence of at least one bound microorganism strain.

Item 66. The method of item 65, wherein the detecting is carried out by a method selected from culture-based methods, microscopy and other imaging methods, genetic detection methods, immunologic detection methods, bioluminescence-based detection methods, and combinations thereof.

Item 67. The method of any one of items 64 to 66, wherein the contacting comprises passing the fluid sample at least once through the laminated article.

Item 68. The method of any one of items 64 to 67, wherein the contacting comprises passing the fluid sample through the laminated article at a pressure of 4.0 pounds per square inch (psi) (27.58 kilopascals (kPa)) or less.

Item 69. The method of any one of items 64 to 68, wherein the contacting comprises passing the fluid sample through the laminated article at a pressure of 0.5 psi (3.4 kPa) or less.

Item 70. The method of any one of items 64 to 69, wherein the microorganism strain is selected from strains of bacteria, fungi, protozoans, viruses, bacterial endospores, and combinations thereof.

Item 71. The method of any one of items 64 to 70, wherein the laminated article reduces the amount of microorganism in the fluid sample by at least a factor of 100.

Item 72. A filtration device comprising:
 a) a container having inlet and outlet ports for liquid passage; and
 b) a laminated article according to any one of items 1 to 29 contained within the container.

Item 73. The laminated article of any one of items 1 to 28, wherein the second substrate is at least partially sealed to the first substrate with a polymeric binder comprising a plurality of polymeric binder fibers.

Item 74. The laminated article of any one of items 1 to 28 or 73, wherein the second substrate is at least partially sealed to the first substrate with a polymeric binder comprising a plurality of polymeric binder particles.

Item 75. The laminated article of item 74, wherein the polymeric binder particles comprise ultra-high molecular weight polyethylene (UHMWPE) particles.

Item 76. The laminated article of item 74 or item 75, wherein the polymeric binder particles comprise spherical particles, particles having surface convolutions, or a combination thereof.

Item 77. The method of any one of items 30 to 63, further comprising depositing a polymeric binder comprising a plurality of polymeric binder fibers, a plurality of polymeric binder particles, or a combination thereof on the first substrate prior to sealing the second substrate to the first substrate.

Item 78. The method of any one of items 30 to 63 or 77, further comprising depositing a polymeric binder comprising a plurality of polymeric binder fibers, a plurality of polymeric binder particles, or a combination thereof on the second substrate prior to sealing the second substrate to the first substrate.

Item 79. The method of any one of items 30 to 63, 77, or 78, further comprising depositing a polymeric binder comprising a plurality of polymeric binder fibers, a plurality of polymeric binder particles, or a combination thereof on the porous fibrous nonwoven matrix having the guanidine-functionalized metal silicate particles prior to sealing the second substrate to the first substrate.

Item 80. The method of any one of items 77 to 79, wherein the polymeric binder comprises a plurality of polymeric binder fibers.

Item 81. The method of any one of items 77 to 80, wherein the polymeric binder comprises a plurality of polymeric binder particles.

Item 82. The method of any one of items 77 to 81, wherein the polymeric binder particles comprise ultra-high molecular weight polyethylene (UHMWPE) particles.

Item 83. The method of item 82, wherein the polymeric binder particles comprise spherical particles, particles having surface convolutions, or a combination thereof.

Item 84. The method of any of items 81 to 83, wherein the polymeric binder particles increase a pressure differential across the laminated article by 0 psi to 0.4 psi, as compared to the same laminated article without the deposited polymeric binder particles.

EXAMPLES

Materials

Materials used in the examples were as indicated in Table 1. All chemicals were purchased from Sigma Aldrich (St. Louis, Mo.) or Fisher Scientific (Pittsburgh, Pa.) unless otherwise noted. Microbiological testing was performed in duplicates with standard deviation less than 10% observed unless otherwise stated.

TABLE 1

| | |
|---|---|
| 0.45 micrometer filters | 47 mm cellulose nitrate filters, 0.45 micrometer pore size, from Sartorius, obtained from Fisher Scientific |
| Butterfield's buffer | Monobasic potassium phosphate buffer obtained from 3M Company, St. Paul, MN as "3M FLIP-TOP DILUTION BOTTLE WITH BUTTERFIELD'S BUFFER" (Catalog Number FTBFD90) |
| CM-111 | Amorphous, spheroidized magnesium silicate particles purchased from 3M Company, St. Paul, MN, as "3M COSMETIC MICROSPHERES" CAS No. 1343-88-0 |
| DI water | deionized, filtered, 18 megaohm water, processed through a MILLI-Q GRADIENT SYSTEM obtained from Millipore, Waltham, MA |
| Endo Agar plate | Premade agar plates, Catalog # G28, purchased from Hardy Diagnostics, Santa Maria, CA |
| Escherichia coli ATCC 11229 | Escherichia coli strain of microorganisms purchased from American Type Culture Collection, Manassas, VA |
| Fiber 1 | Short fibrillated polyethylene fibers, obtained from Minifibers, Inc., Johnson City, TN, under the trade designation "SHORT STUFF POLYETHYLENE" |
| Fiber 2 | 1 denier 12.7 mm long chopped nylon fibers, obtained from Minifibers, Inc., Johnson City, TN |
| Fiber 3 | 2 denier 5 mm long bicomponent ethylene vinyl acetate/polypropylene fibers, obtained from Minifibers, Inc., Johnson City, TN |
| Fiber 4 | long glass fibers, obtained from Schuller, Inc., Denver, CO, under the trade designation "MICRO-STRAND 106-475 GLASS FIBERGLAS" |
| Lamination Substrate 1 ("L-1") | REEMAY 2030 POLYESTER (PET) spunbond, 79.7 grams per square meter ("gsm"), obtained from Fiberweb, UK |
| Lamination Substrate 2 ("L-2") | REEMAY 2214 POLYESTER (PET) spunbond, 45.8 gsm from Fiberweb, UK |
| Lamination Substrate 3 ("L-3") | REEMAY 2295 POLYESTER (PET) spunbond, 100 gsm, obtained from Fiberweb, UK |
| Lamination Substrate 4 ("L-4") | Polyamide polyester (PA6/PET) bicomponent spunbond, 80 gsm, obtained from Baiksan Lintex, Gyunggi South Korea |
| Lamination Substrate 5 ("L-5") | Polyamide polyester (PA6/PET) bicomponent spunbond, 60 gsm, obtained from Baiksan Lintex, Gyunggi, South Korea |
| Lamination Substrate 6 ("L-6") | Hydrophilic Polypropylene (PP) spunbond, 80 gsm, obtained from Don and Low, Scotland, UK |
| TSA plate | plates prepared according to manufacturer's instructions with 3 wt % Tryptic Soy Agar powder purchased from BD (DIFCO), Sparks, MD |
| TSB | broth prepared according to manufacturer's instructions with 3.7 wt % Tryptic Soy Broth powder purchased from BD (DIFCO), Sparks, MD |

Preparation of Plasma-Treated Lamination Substrates "L1$_{PT}$", "L2$_{PT}$", and "L3$_{PT}$"

Commercially obtained lamination substrates L-1, L-2, and L-3 were each separately plasma-treated on a plasma treatment apparatus, to provide plasma-treated lamination substrates "L1$_{PT}$", "L2$_{PT}$", and "L3$_{PT}$", respectively. The plasma treatment apparatus had rotating drum electrodes powered by a radio frequency ("RF") power source, a grounded chamber that acted as a grounded electrode, an unwinder roll that continuously supplied lamination substrate to be treated. The rotating drum electrodes were powered by a 1000 watt RF power supply. The chamber was vacuum pumped, in which the base pressure was about 990 millitorr ("mTorr") (132 Pascals ("Pa")) or less. Process gases were metered into the chamber. The flow rate of each process gas was 500 standard cubic centimeters per minute ("SCCM") of oxygen (O$_2$) and 3500 SCCM of air containing 70 SCCM of silicon tetrahydride (SiH$_4$), respectively. Pressure in the chamber was controlled independently from flow rate of the process gases by a butterfly valve. The feed rate of the web was 5 to 20 ft/min. (1.5 to 6.1 meters per minute). The plasma treatment apparatus included a winder roll, to collect plasma-treated lamination substrate.

Preparative Examples 1 to 4 (PE-1 to PE-4):
Preparation of Guanidine-Functionalized Particles A mixture of O-methylisourea hemisulfate (12.9 g, 105 mmol) in anhydrous methanol (100 g) was treated with 3-aminopropyltrimethoxysilane (18.8 g, 105 mmol) and stirred for 2 days, to provide a reagent solution. Next, 12.0 g portions of this reagent solution were transferred to each of three 8 oz. screw cap jars and each sample was diluted with 90 mL of anhydrous methanol. 10.0 g portions of CM-111 (i.e., magnesium silicate) particles were added to each jar, followed by differing amounts of water, as shown in Table 2 (below). The jars were sealed with polytetrafluoroethylene-lined caps and the mixture in each jar was stirred for 2 days. The resulting guanidine-functionalized amorphous, spheroidized magnesium silicate particles were isolated by filtration, rinsed with methanol and allowed to air dry, to provide guanidine-functionalized magnesium silicate particles, PE-1 to PE-4. The amounts of water added and results for XPS testing (i.e., elements present at a detectable level by XPS on the surface of the guanidine-functionalized magnesium silicate particles, reported as "atomic percent N") and nitrogen combustion analysis ("% N") are summarized in Table 2:

TABLE 2

| Example No. | Equivalents of water relative to 3-aminopropyltrimethoxysilane | Atomic percent N (XPS) | % N (Combustion analysis) | Ratio of atomic percent N to atomic percent Si (XPS) |
| --- | --- | --- | --- | --- |
| PE-1 | 0.25 | 1.5-1.7 | <L.D.* | 0.07 |
| PE-2 | 0.5 | 2.8-3.1 | <L.D.* | 0.14 |
| PE-3 | 1.0 | 7.3-8.0 | 0.92 | 0.42 |
| PE-4 | 2.0 | 7.3-8.0 | 2.21 | 0.53 |

*<L.D. = below the limit of detection.

Preparative Examples 5 to 8 (PE-5 to PE-8):
Preparation of Wetlaid Nonwoven Articles Four fiber premixes for each of Preparative Examples PE-1 to PE-4 in Table 3 below were prepared by mixing various amounts of commercially obtained Fiber 1 ("F1"), Fiber 2 ("F2"), Fiber 3 ("F3"), and Fiber 4 ("F4"), as shown in Table 3 below. Fibers F1-F4 were added in the indicated amounts to 3 liters of cold deionized water in a 4 L blender (available from VWR, Radnor, Pa., under the trade designation "WARING COMMERCIAL HEAVY DUTY BLENDER, MODEL 37BL84") and blended at low speed for 30 seconds. Each mixture was examined for uniform dispersion of the fibers without nits or clumps. The additive from the indicated Preparative Example (i.e., guanidine-functionalized particles from one of Preparative Examples PE-1 to PE-4; see Table 3 for amounts) was added with an additional liter of deionized water and mixed at low speed for 15 seconds.

TABLE 3

| | Material | | | | |
| --- | --- | --- | --- | --- | --- |
| Prep. Ex. No. | F1, grams | F2, grams | F3, grams | F4, grams | Additive, grams, of Prep. Ex. No. |
| PE-5 | 11.01 | 3.01 | 2.25 | 1.76 | 5.07 g of PE-1 |
| PE-6 | 11.01 | 3.01 | 2.25 | 1.76 | 5.10 g of PE-2 |
| PE-7 | 11.01 | 3.02 | 2.25 | 1.78 | 5.00 g of PE-3 |
| PE-8 | 11.01 | 3.01 | 2.26 | 1.76 | 5.04 g of PE-4 |

For each mixture in Table 3, a felt was prepared using a pad maker apparatus (obtained from Williams Apparatus, Watertown, N.Y., under the trade designation "TAPPI") that had a box measuring about 30 centimeters square and 30 centimeters high with a fine mesh screen at the bottom and a drain valve. The box was filled with tap water up to a height of about 1 centimeter above the screen. Each fiber and additive mixture was poured into the box and the valve was opened immediately which created a vacuum that pulled the water out of the box. The resulting wet-laid felt was approximately 0.8-1 millimeter thick.

The wet-laid felt was transferred from the apparatus onto a 20 centimeter square sheet of blotter paper (96-pound white paper, obtained from Anchor Paper, St. Paul, Minn.). The felt was sandwiched between 2 to 4 layers of blotter paper, to blot excess water. The pressed felt was then transferred onto a fresh sheet of blotter paper and placed in an oven (obtained from SPX Thermal Product Solutions, White Deer, Pa., under the trade designation "BLUE M STABIL-THERM OVEN, MODEL OV-560A2") set at 110° C. for about 2.5 hrs to remove residual water and to form a porous wetlaid nonwoven matrix ("wetlaid nonwoven").

Examples 1 to 9 (EX-1 to EX-9): Preparation of Ultrasonically Laminated Articles Ultrasonic welding to form the laminated articles of EX-1 to EX-9 was conducted with a BRANSON 2000d ULTRASONIC WELDER. The ultrasonic welder had an aluminum cylindrical ultrasonic horn, with a ring at the working end. The ring had an outer diameter of 47 mm and an inner diameter of 41 mm. Ultrasonic welds were conducted against a flat aluminum plate. The ultrasonic welding conditions used a 1:1.5 gain booster, 90 psi (0.62 MPa) cylinder force, force trigger of 50 pounds (23 kg), welding amplitude of 100% with an end-of-weld hold time of 0.2 seconds. Weld settings (joules) for each of EX-1 to EX-9 were as indicated in Table 2. The wetlaid nonwoven material indicated in Table 4 (i.e., one of PE-4 to PE-7) was placed between two layers of the indicated lamination substrate to provide a layered structure, and the welder was started. The horn descended to compress the layered structure, and when the trigger force was met, the ultrasonic vibrations were started. The ultrasonication was stopped at the target energy setting, and the ultrasonicated sample was contained during the hold time.

TABLE 4

| Example No. | Lamination Substrate No. | Wetlaid Nonwoven Sample No. | Weld Setting |
|---|---|---|---|
| EX-1 | L-1 | PE-5 | 250 joules |
| EX-2 | L-2 | PE-5 | 250 joules |
| EX-3 | L-3 | PE-6 | 250 joules |
| EX-4 | L-4 | PE-6 | 150 joules |
| EX-5 | L-5 | PE-7 | 150 joules |
| EX-6 | L-6 | PE-7 | 200 joules |
| EX-7 | $L1_{PT}$ | PE-8 | 250 joules |
| EX-8 | $L2_{PT}$ | PE-7 | 250 joules |
| EX-9 | $L3_{PT}$ | PE-8 | 250 joules |

Bacterial Testing of Ultrasonically Laminated Articles
Preparation of a Water "Pre-Filtration" Test Sample A streaked culture of *E. coli* (ATCC 11229) on a TSA plate was incubated overnight at 37° C. From the plate an isolated colony was removed and inoculated into 5 mL of TSB using a standard microbiology loop and incubated in a shaking incubator (INNOVA® 44 from New Brunswick Scientific) at 37° C. for 20-22 hours. The overnight culture that contained ~2-3×10$^9$ colony forming units per milliliter ("CFU/mL") was serially diluted in Butterfield's Buffer to obtain an inoculum with approximately 1×10$^6$ CFU/mL.

A "pre-filtration" test sample was then prepared by inoculating 200 mL of DI water with a 1:100 dilution of the 10$^6$ CFU/mL inoculum, resulting in the "pre-filtration" test sample containing approximately 10$^4$ CFU/mL (~4 Log CFU/mL).

Example 10

A filter disk 47 mm in diameter was die punched from the laminated wetlaid (i.e., the laminate that contained wetlaid nonwoven matrix) of Example 1 and was placed into a sample holder, which was a custom device fabricated from polycarbonate. The device had three parts and was cylindrically shaped measuring about 60 mm in diameter by about 45 mm high. A lower part of the device contained a support screen for supporting the filter disk, and a sample outlet port. The top portion of the device was enclosed except for the sample inlet port, which was connect through PVC tubing to a Cole Parmer peristaltic pump, and was vented on the upstream side to allow for purging with air. O-ring seals were used to prevent leakage on both the upstream and downstream sides of the device. Internal threads provided closure pressure. The 47 mm filter disk was placed on top of the support screen, an O ring was added on top, and holder was closed.

Laminated wetlaids were tested in duplicates. A "pre-filtration" sample was pumped through the sample holder containing the laminated wetlaid disk using a Cole Parmer peristaltic pump (MODEL NO. 7553-70) using ⅛" (3.2 mm) wall thick PVC tubing (VWR catalog #60985-522). The spiked water was pumped through the laminated wetlaid disk at a flow rate of 12 mL/minute. Filtrates were collected in 250 mL sterile glass bottles. The first 100 mL filtrate was collected and discarded. The second 100 mL filtrate was collected for further processing.

After each filtration test, the holder was disassembled to remove the laminated wetlaid filter disk using sterile forceps. Between testings of laminated wetlaid filter disks, the filtration device was rinsed with 500 mL of filtered-sterilized deionized water.

A 10 mL volume of the second 100 mL filtrate was added to a 100 mL flip-top bottle containing Butterfield's Buffer to obtain a 1:10 dilution. The bottle was capped and mixed manually by shaking for 10 seconds. A 10 mL volume was removed and added to another 100 mL flip-top bottle to obtain a 1:100 dilution. Similarly, the filtrate was further diluted to 1:1000 and 1:10000. These 100 mL diluted filtrates were each vacuum filtered through separate 0.45 micrometer filters. After each filtration, the vacuum apparatus was rinsed with filtered sterilized 500 mL deionized water and blotted dry with laboratory wipes ("KIM-WIPES").

Each of the 0.45 micrometer filters was then removed from the apparatus with sterile forceps plates and placed on a separate Endo Agar plate, grid side up. The plates were incubated at 37° C. for 18 to 20 hours. Colony counts were obtained from the plates by manual counting. The CFU/mL colony counts were then converted to "Log CFU/mL in filtrate sample" values.

For each of the filtration examples in EX-10 to EX-18, a corresponding "pre-filtration" sample was also diluted and filtered through a 0.45 micrometer filter, and the 0.45 micrometer cellulose nitrate filter disks was then removed from the apparatus with sterile forceps plates and placed on an Endo Agar plates, grid side up. The plates were incubated at 37° C. for 18 to 20 hours. Colony counts were obtained from the plates by manual counting. The CFU/mL colony counts were converted to "Log CFU/mL in pre-filtration sample" values.

Log Reduction Values ("LRV") were calculated based on counts obtained from the plated filtrate and pre-filtration samples by using the formula below:

LRV=(Log of CFU/mL in pre-filtration sample)−(Log of CFU/mL in filtrate sample)

Similar filtration testing was done on 47 mm disks of Examples 11 to 18. Filtration results were as listed in Table 5.

Comparative Examples 1 to 3 (CE-1 to CE-3) were performed very similarly to Examples EX-10 to EX-18, except that instead of using the laminated articles, only unlaminated wetlaid nonwoven material was used, as indicated in Table 5. The comparative examples CE-1 to CE-3 thus offered a comparison to observe whether inclusion of lamination substrate materials interfered with filtration capability of unlaminated wetlaid nonwoven materials.

TABLE 5

| Filtration Testing Example No. | Ultrasonically Laminated Material | Lamination Substrate No. | Wetlaid Nonwoven Sample No. | Log CFU in "pre-filtration" sample | LRV |
|---|---|---|---|---|---|
| EX-10 | EX-1 | L-1 | PE-5 | 4.29 | 0.50 |
| EX-11 | EX-2 | L-2 | PE-5 | 4.29 | 0.37 |
| EX-12 | EX-3 | L-3 | PE-6 | 4.29 | 1.96 |

TABLE 5-continued

| Filtration Testing Example No. | Ultrasonically Laminated Material | Lamination Substrate No. | Wetlaid Nonwoven Sample No. | Log CFU in "pre-filtration" sample | LRV |
|---|---|---|---|---|---|
| EX-13 | EX-4 | L-4 | PE-6 | 4.29 | 4.15 |
| EX-14 | EX-5 | L-5 | PE-7 | 4.29 | 3.67 |
| EX-15 | EX-6 | L-6 | PE-7 | 4.29 | 3.76 |
| EX-16 | EX-7 | $L1_{PT}$ | PE-8 | 3.47 | 3.19* |
| EX-17 | EX-8 | $L2_{PT}$ | PE-7 | 3.55 | 3.55 |
| EX-18 | EX-9 | $L3_{PT}$ | PE-8 | 3.47 | 3.09** |
| CE-1 | — | — | PE-5 | 3.45 | 3.33 |
| CE-2 | — | — | PE-6 | 3.45 | 3.45 |
| CE-3 | — | — | PE-7 | 3.60 | 3.60 |

*the LRV value had ~12% standard deviation;
**the LRV value had ~17% standard deviation;
all other LRV values had <10% standard deviation.

Turbidity Test

The Turbidity Test is based on the "Standard for Hygienic Safety Evaluation of Equipment and Protective Materials in Drinking Water," (standard number GB/T 17219-1998) and is as follows: A 47 mm disk of a laminated sample is placed in a 2.5 liter vacuum filtration apparatus (with a side arm) and flushed continuously with DI water for 30 minutes. The sample is then removed and placed in a glass jar containing 70 mL DI water for 24 hours. Water sample aliquots are analyzed for turbidity using a turbidimeter, such as a MICRO 100 TURBIDIMETER (available from HF scientific, Fort Myers, Fla.). Out of the 70 mL sample 2 samples of 25 mL are used for turbidity measurements. A volume of 70 mL of DI water serves as control.

Examples 19 to 22 (EX-19 to EX-22): Turbidity Testing of Ultrasonically Laminated Articles In accordance with the Turbidity Test above, 47 mm disks of laminated samples from EX-3 to EX-6 were each placed in a 2.5 liter vacuum filtration apparatus (with a side arm) and flushed continuously with DI water for 30 minutes. Samples were then removed and placed in glass jars containing 70 mL DI water for 24 hours. Water samples were analyzed for turbidity using a MICRO 100 TURBIDIMETER (available from HF scientific, Fort Myers, Fla.). Out of the 70 mL sample 2 samples of 25 mL were used for turbidity measurements. A volume of 70 mL of DI water served as control. The turbidity measurements were as listed in Table 6 below.

TABLE 6

| Turbidity Example No. | Wetlaid Example No. | Turbidity (NTUs) |
|---|---|---|
| EX-19 | EX-3 | 0.26 |
| EX-20 | EX-4 | 0.10 |
| EX-21 | EX-5 | 0.08 |
| EX-22 | EX-6 | 0.17 |
| DI water (Control) | N/A | 0.02 |

Example 23: Preparation of an Ultrasonically Laminated Sheet Article

A rectangular laminated article, having dimensions of 28 cm by 13 cm for the sealed area, was prepared from L4 lamination substrate, sealing all four sides of the rectangle with a BRANSON 2000d ultrasonic welder. The ultrasonic horn was a 14.25 inch (36 cm) long bar horn that has a 0.25 inch (6.3 mm) wide welding face. A fine knurled 0.125 inch (3.2 mm) wide anvil was used beneath the lamination while a silicone coated paper was placed between the horn and the lamination. The welding conditions used a 1:1.5 gain booster, 90 psi (0.62 MPa) cylinder force, a force trigger of 100 lbs. (46 kg), and a welding amplitude of 100%, with an end of weld hold time of 0.2 seconds. The weld setting for the long sides was 400 joules, and the weld setting for the short sides was 200 joules.

Example 24

Another rectangular laminated article was prepared as in Example 23, except for using L5 lamination substrate, and sealing along only one of the long sides of the rectangle, in addition to sealing along both of the short sides of the rectangle.

Example 25 (Prophetic): Preparation of a Laminated Sheet Article with a Layer of Thermoplastic Binder Fibers A fiber premix is prepared by mixing various amounts of Fiber 1, Fiber 2, Fiber 3, and Fiber 4 as shown in Table 7 below. The fibers are added to 3 liters of cold DI water in a 4 L blender (available from VWR, Radnor, Pa., under the trade designation "WARING COMMERCIAL HEAVY DUTY BLENDER, MODEL 37BL84") and blended at low speed for 30 seconds. The mixture is examined for uniform dispersion of the fibers without nits or clumps. The additive from Preparatory Example 6 is added with an additional liter of DI water and mixed at low speed for 15 seconds.

A felt is prepared using a pad maker apparatus (obtained from Williams Apparatus, Watertown, N.Y., under the trade designation "TAPPI") that has a box measuring about 30 centimeters (12 inches) square and 30 centimeters (12 inches) high with a fine mesh screen at the bottom and a drain valve. On the screen ~a 14 (36 cm) inch×12 inch (30 cm) piece of a polyethylene spunbond (PET Lutradur 7240 obtained from Fiberweb, Cincinnati, Ohio) is laid as scrim on the screen. The box is filled with tap water up to a height of about 1 centimeter above the screen. The mixture is poured into the box and the valve is opened immediately which creates a vacuum that pulls the water out of the box. The resulting wet-laid felt is approximately 0.8-1 millimeter thick.

Five grams of Fiber 3 are manually spread on top of the formed wet-laid felt including along the perimeter of the felt.

The wet-laid felt is then covered with a 14 inch×12 inch piece of Lamination Substrate 4. The scrim is pressed onto the felt using a heavy rolling pin. The wet-laid felt is transferred from the apparatus onto a 20 centimeter square sheet of blotter paper (96-pound white paper, obtained from Anchor Paper, St. Paul, Minn.). The felt is sandwiched between 2 to 4 layers of blotter paper, to blot excess water. The sandwiched felt is flipped over and the polyethylene spunbond scrim is removed. Five grams of Fiber 3 are also added on top of this side of the wet-laid and covered with another 14 inch×12 inch piece of Lamination Substrate 4. The felt is pressed again with a heavy rolling pin and is then transferred onto a fresh sheet of blotter paper and placed in an oven (obtained from SPX Thermal Product Solutions, White Deer, Pa., under the trade designation "BLUE M STABIL-THERM OVEN, MODEL OV-560A2") set at 110° C. for about 3 hours to remove residual water and to form a porous wet-laid matrix laminated on both sides.

TABLE 7

| Material (grams) | Example 59 |
|---|---|
| Fiber 8 | 11.00 |
| Fiber 2 | 3.00 |
| Fiber 3 | 2.25 |
| Fiber 4 | 1.75 |
| Additive (PE-6) | 5.00 |

While the specification has described in detail certain exemplary embodiments, it will be appreciated that those skilled in the art, upon attaining an understanding of the foregoing, may readily conceive of alterations to, variations of, and equivalents to these embodiments. Furthermore, all publications and patents referenced herein are incorporated by reference in their entirety to the same extent as if each individual publication or patent was specifically and individually indicated to be incorporated by reference. Various exemplary embodiments have been described. These and other embodiments are within the scope of the following claims.

What is claimed is:

1. A laminated article comprising:
a) a porous fibrous nonwoven matrix;
b) a plurality of guanidine-functionalized metal silicate particles enmeshed within the porous fibrous nonwoven matrix, the guanidine-functionalized metal silicate particles comprising:
a metal silicate particle that is modified with at least one silane having the formula $$X_{3-n}R^a{}_nSi\text{—}Y\text{-}G,$$

wherein:
n is 0, 1, or 2;
each $R^a$, if present, is independently an alkyl, aralkyl, or aryl;
Y is a divalent group comprising an alkylene having 2 to 20 carbons;
G is a guanidine group of the formula —NH—C(=NH)—NH$_2$; and
each X is independently alkoxy or acyloxy;
c) a first substrate; and
d) a second substrate sealed to the first substrate along at least a portion of a perimeter of the first substrate, wherein the porous fibrous nonwoven matrix is disposed between the first substrate and the second substrate.

2. The laminated article of claim 1, wherein the first substrate and the second substrate are independently selected from a spunbond polypropylene, a spunbond polyamide, a spunbond blend of polyamide and polyester, a spunbond polyethylene, a spunbond polyester, a spunbond polybutylene terephthalate, and a spunbond polypropylene.

3. The laminated article of claim 1, wherein the first substrate and the second substrate independently comprise a spunbond material comprising a gram per square meter basis weight (gsm) of 10 to 200 gsm, inclusive.

4. The laminated article of claim 1, wherein the laminated article provides a turbidity of less than 0.2 nephelometric turbidity units (NTU) according to the Turbidity Test.

5. The laminated article of claim 1, wherein the metal silicate particle is a magnesium silicate particle.

6. The laminated article of claim 1, wherein each of the first substrate and the second substrate is liquid permeable.

7. A method of making a laminated article, the method comprising:
a) providing a plurality of fibers;
b) providing a plurality of guanidine-functionalized metal silicate particles;
c) mixing the plurality of guanidine-functionalized metal silicate particles and the plurality of fibers together to form a porous fibrous nonwoven matrix having the guanidine-functionalized metal silicate particles enmeshed within the porous fibrous nonwoven matrix;
d) providing a first substrate;
e) providing a second substrate;
f) disposing the porous fibrous nonwoven matrix having the guanidine-functionalized metal silicate particles between the first substrate and the second substrate; and
g) sealing the second substrate to the first substrate along at least a portion of a perimeter of the first substrate.

8. The method of claim 7, wherein the providing a plurality of guanidine-functionalized metal silicate particles comprises:
i) reacting an O-methylisourea salt with a linker comprising the formula $$X_{3-n}R^a{}_nSi\text{—}Y\text{—}NH_2,$$

wherein:
n is 0, 1, or 2;
each $R^a$, if present, is independently an alkyl, aralkyl, or aryl;
Y is a divalent group comprising an alkylene having 2 to 20 carbons; and
each X is independently alkoxy or acyloxy;
to form a guanidine-functionalized linker; and
ii) forming a mixture of the guanidine-functionalized linker and metal silicate particles, such that the guanidine-functionalized linker reacts with hydroxyl groups of the metal silicate particles to form covalent bonds between the guanidine-functionalized linker and the metal silicate particles, thereby forming the guanidine-functionalized metal silicate particles.

9. The method of claim 7, wherein the sealing is performed using ultrasonic sealing, heat sealing, adhesive sealing, stitching, or a combination thereof.

10. The method of claim 7, further comprising mixing at least one polymeric binder together with the plurality of guanidine-functionalized metal silicate particles and the plurality of fibers.

11. A method of removing microorganisms from a fluid sample, the method comprising:
a) providing a laminated article, the laminated article comprising:
1) a porous fibrous nonwoven matrix;
2) a plurality of guanidine-functionalized metal silicate particles enmeshed within the porous fibrous nonwoven matrix, the guanidine-functionalized metal silicate particles comprising:
a metal silicate particle that is modified with at least one silane having the formula $$X_{3-n}R^a{}_n Si\text{—}Y\text{-}G$$

wherein:
n is 0, 1, or 2;
each $R^a$, if present, is independently an alkyl, aralkyl, or aryl;
Y is a divalent group comprising an alkylene having 2 to 20 carbons;
G is a guanidine group of the formula —NH—C(=NH)—NH$_2$; and
each X is independently alkoxy or acyloxy;
3) a first substrate; and
4) a second substrate sealed to the first substrate along at least a portion of a perimeter of the first substrate, wherein the porous fibrous nonwoven matrix is disposed between the first substrate and the second substrate;
b) providing a fluid sample containing at least one microorganism strain; and
c) contacting the fluid sample with the laminated article such that at least a portion of the at least one microorganism strain is removed from the fluid sample.

12. The method of claim 11, wherein the contacting comprises passing the fluid sample at least once through the laminated article.

13. The method of claim 12, wherein the contacting comprises passing the fluid sample through the laminated article at a pressure of 4.0 pounds per square inch (psi) (27.58 kilopascals (kPa)) or less.

14. The method of claim 11, wherein the laminated article reduces the amount of microorganism in the fluid sample by at least a factor of 100.

15. A filtration device comprising:
a) a container having inlet and outlet ports for liquid passage; and
b) a laminated article contained within the container, the laminated article comprising:
1) a porous fibrous nonwoven matrix;
2) a plurality of guanidine-functionalized metal silicate particles enmeshed within the porous fibrous nonwoven matrix, the guanidine-functionalized metal silicate particles comprising:
a metal silicate particle that is modified with at least one silane having the formula $$X_{3-n}R^a{}_n Si\text{—}Y\text{-}G$$

wherein:
n is 0, 1, or 2;
each $R^a$, if present, is independently an alkyl, aralkyl, or aryl;
Y is a divalent group comprising an alkylene having 2 to 20 carbons;
G is a guanidine group of the formula —NH—C(=NH)—NH$_2$; and
each X is independently alkoxy or acyloxy;
3) a first substrate; and
4) a second substrate sealed to the first substrate along at least a portion of a perimeter of the first substrate, wherein the porous fibrous nonwoven matrix is disposed between the first substrate and the second substrate.

* * * * *

UNITED STATES PATENT AND TRADEMARK OFFICE
CERTIFICATE OF CORRECTION

PATENT NO. : 10,308,669 B2
APPLICATION NO. : 15/037132
DATED : June 4, 2019
INVENTOR(S) : Manjiri Kshirsagar It is certified that error appears in the above-identified patent and that said Letters Patent is hereby corrected as shown below:

In the Specification

<u>Column 4</u>,
Line 47, delete "Si—O-bond;" and insert -- Si—O— bond; --, therefor.

<u>Column 10</u>,
Lines 7 and 8, delete "-aminoundecyl-trimethoxysilane ("SIA05951.0")," and insert
-- -aminoundecyltrimethoxysilane ("SIA0595.0"), --, therefor.

<u>Column 12</u>,
Line 12, delete "poly(l-butene)," and insert -- poly(1-butene), --, therefor.

In the Claims

<u>Column 37</u>,
Line 14, in Claim 11, delete "$X_{3-n}R^a_nSi$—Y-G" and insert -- $X_{3-n}R^a_nSi$—Y-G, --, therefor.

<u>Column 38</u>,
Line 20, in Claim 15, delete "$X_{3-n}R^a_nSi$—Y-G" and insert -- $X_{3-n}R^a_nSi$—Y-G, --, therefor.

Signed and Sealed this
Thirtieth Day of July, 2019

Andrei Iancu
*Director of the United States Patent and Trademark Office*